US010932867B2

(12) United States Patent
Park

(10) Patent No.: US 10,932,867 B2
(45) Date of Patent: Mar. 2, 2021

(54) REUSABLE SURGICAL INSTRUMENT WITH SINGLE-USE TIP AND INTEGRATED TIP COVER

(71) Applicant: Intuitive Surgical Operations, Inc., Sunnyvale, CA (US)

(72) Inventor: William J. Park, San Jose, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 474 days.

(21) Appl. No.: 14/911,233

(22) PCT Filed: Aug. 14, 2014

(86) PCT No.: PCT/US2014/051098
§ 371 (c)(1),
(2) Date: Feb. 9, 2016

(87) PCT Pub. No.: WO2015/023865
PCT Pub. Date: Feb. 19, 2015

(65) Prior Publication Data
US 2016/0175060 A1 Jun. 23, 2016

Related U.S. Application Data

(60) Provisional application No. 61/866,127, filed on Aug. 15, 2013.

(51) Int. Cl.
*A61B 34/30* (2016.01)
*A61B 17/00* (2006.01)
(Continued)

(52) U.S. Cl.
CPC .............. *A61B 34/30* (2016.02); *A61B 17/00* (2013.01); *A61B 2017/0023* (2013.01);
(Continued)

(58) Field of Classification Search
CPC . A61B 34/35; A61B 17/00; A61B 2017/0023; A61B 2034/301;
(Continued)

(56) References Cited

U.S. PATENT DOCUMENTS

| 5,052,402 A | 10/1991 | Bencini et al. |
| 5,395,375 A | 3/1995 | Turkel et al. |

(Continued)

FOREIGN PATENT DOCUMENTS

| CA | 2853431 A1 | 5/2013 |
| CN | 102783982 A | 11/2012 |

(Continued)

OTHER PUBLICATIONS

International Search Report and Written Opinion for Application No. PCT/US14/51098, dated Nov. 20, 2014, 10 pages.
(Continued)

*Primary Examiner* — Thomas A Giuliani
*Assistant Examiner* — Christine A Dedoulis

(57) ABSTRACT

A surgical instrument (203) includes a reusable instrument portion (204) and a disposable tip assembly (205). The disposable tip assembly (205) includes an end effector assembly (206) that in turn includes an end effector. The disposable tip assembly (205) also includes a locking tip cover (410) that locks the disposable tip assembly (205) to a lock interface element (448B) of a tip interface (245) of the reusable instrument portion (204). To facilitate mounting the disposable tip assembly (205) on the tip interface (245) of the reusable instrument portion (204), the disposable tip assembly (205) includes a first quick connect/disconnect element (409) and the tip interface (245) includes a second quick connect/disconnect element (447). The second quick connect/disconnect element (447) is coupled to a tendon (452). The tendon (452) is also coupled to an actuator assembly that provides forces that push and pull (push/pull) the tendon.

20 Claims, 10 Drawing Sheets

(51) Int. Cl.
*A61B 18/00* (2006.01)
*A61B 18/14* (2006.01)

(52) U.S. Cl.
CPC ............ *A61B 2017/00473* (2013.01); *A61B 2017/00477* (2013.01); *A61B 2018/00178* (2013.01); *A61B 2018/146* (2013.01); *A61B 2034/301* (2016.02)

(58) Field of Classification Search
CPC ........... A61B 2017/00584; A61B 2017/00464; A61B 18/1445; A61B 34/30; A61B 2017/00473; A61B 2017/0477; A61B 2018/00178; A61B 2018/146; B60K 2015/0451
See application file for complete search history.

(56) References Cited

U.S. PATENT DOCUMENTS

| | | | |
|---|---|---|---|
| 5,396,900 | A | 3/1995 | Slater et al. |
| 5,482,054 | A | 1/1996 | Slater et al. |
| 5,496,347 | A | 3/1996 | Hashiguchi et al. |
| 5,527,339 | A | 6/1996 | Koscher et al. |
| 5,582,617 | A | 12/1996 | Klieman et al. |
| 5,593,402 | A | 1/1997 | Patrick |
| 5,749,881 | A | 5/1998 | Sackier et al. |
| 5,792,165 | A | 8/1998 | Klieman et al. |
| 5,855,583 | A | 1/1999 | Wang et al. |
| 5,906,630 | A | 5/1999 | Anderhub et al. |
| 5,964,780 | A | 10/1999 | Balazs |
| 5,968,074 | A | 10/1999 | Prestel |
| 6,206,903 | B1 | 3/2001 | Ramans |
| 6,273,860 | B1 | 8/2001 | Kostylev et al. |
| 6,309,397 | B1 | 10/2001 | Julian et al. |
| 6,331,181 | B1 | 12/2001 | Tierney et al. |
| 6,394,998 | B1 | 5/2002 | Wallace et al. |
| 6,554,844 | B2 | 4/2003 | Lee et al. |
| 6,663,641 | B1 | 12/2003 | Kovac et al. |
| 6,685,698 | B2 | 2/2004 | Morley et al. |
| 6,817,974 | B2 | 11/2004 | Cooper et al. |
| 6,840,938 | B1 | 1/2005 | Morley et al. |
| 6,860,878 | B2 | 3/2005 | Brock |
| 6,994,708 | B2 | 2/2006 | Manzo |
| 7,083,571 | B2 | 8/2006 | Wang et al. |
| 7,125,403 | B2 | 10/2006 | Julian et al. |
| 7,367,973 | B2 * | 5/2008 | Manzo .................. A61B 18/14 604/22 |
| 7,608,083 | B2 | 10/2009 | Lee et al. |
| 7,824,401 | B2 | 11/2010 | Manzo et al. |
| 7,935,130 | B2 | 5/2011 | Williams et al. |
| 8,221,449 | B2 | 7/2012 | Gadberry et al. |
| 8,479,969 | B2 | 7/2013 | Shelton, IV et al. |
| 8,551,115 | B2 | 10/2013 | Steger et al. |
| 8,602,288 | B2 | 12/2013 | Shelton, IV et al. |
| 8,628,518 | B2 | 1/2014 | Blumenkranz et al. |
| 8,800,838 | B2 | 8/2014 | Shelton, IV et al. |
| 9,028,494 | B2 | 5/2015 | Shelton, IV et al. |
| 9,078,684 | B2 | 7/2015 | Williams |
| 9,138,284 | B2 * | 9/2015 | Krom .................. A61B 18/1445 |
| 9,204,923 | B2 | 12/2015 | Manzo et al. |
| 9,339,341 | B2 | 5/2016 | Cooper |
| 9,358,031 | B2 | 6/2016 | Manzo et al. |
| 9,456,839 | B2 | 10/2016 | Cooper et al. |
| 9,918,731 | B2 | 3/2018 | Cooper et al. |
| 10,130,366 | B2 | 11/2018 | Shelton, IV et al. |
| 2004/0260198 | A1 | 12/2004 | Rothberg et al. |
| 2005/0059960 | A1 | 3/2005 | Simaan et al. |
| 2005/0216033 | A1 * | 9/2005 | Lee .................. A61B 17/0469 606/130 |
| 2006/0074415 | A1 | 4/2006 | Scott et al. |
| 2006/0079884 | A1 * | 4/2006 | Manzo ............... A61B 18/1442 606/41 |
| 2006/0184161 | A1 | 8/2006 | Maahs et al. |
| 2007/0005002 | A1 | 1/2007 | Millman et al. |
| 2008/0021278 | A1 * | 1/2008 | Leonard ............ A61B 17/1608 600/129 |
| 2008/0046122 | A1 | 2/2008 | Manzo et al. |
| 2008/0065102 | A1 | 3/2008 | Cooper et al. |
| 2008/0065105 | A1 | 3/2008 | Larkin et al. |
| 2008/0103491 | A1 | 5/2008 | Omori et al. |
| 2008/0196533 | A1 | 8/2008 | Bergamasco et al. |
| 2008/0243106 | A1 | 10/2008 | Coe et al. |
| 2009/0088774 | A1 | 4/2009 | Swarup et al. |
| 2009/0131975 | A1 | 5/2009 | Ahlberg et al. |
| 2009/0198272 | A1 | 8/2009 | Kerver et al. |
| 2009/0326530 | A1 | 12/2009 | Orban, III et al. |
| 2010/0016852 | A1 * | 1/2010 | Manzo ............... A61B 18/1445 606/46 |
| 2010/0198218 | A1 | 8/2010 | Manzo |
| 2010/0318101 | A1 | 12/2010 | Choi |
| 2011/0015650 | A1 | 1/2011 | Choi et al. |
| 2011/0295269 | A1 | 12/2011 | Swensgard et al. |
| 2011/0295270 | A1 | 12/2011 | Giordano et al. |
| 2012/0010611 | A1 * | 1/2012 | Krom .................. A61B 18/1445 606/41 |
| 2012/0010628 | A1 | 1/2012 | Cooper et al. |
| 2012/0116433 | A1 * | 5/2012 | Houser ............... A61B 17/2812 606/169 |
| 2012/0123441 | A1 | 5/2012 | Au et al. |
| 2012/0232338 | A1 * | 9/2012 | Livneh ............... A61B 18/1445 600/104 |
| 2012/0292366 | A1 | 11/2012 | Nalagatla et al. |
| 2013/0046318 | A1 | 2/2013 | Radgowski et al. |
| 2014/0005678 | A1 | 1/2014 | Shelton, IV et al. |
| 2014/0243850 | A1 | 8/2014 | Sadaka |
| 2015/0150635 | A1 | 6/2015 | Kilroy et al. |
| 2015/0157355 | A1 | 6/2015 | Price et al. |
| 2015/0257816 | A1 * | 9/2015 | Ineson ............... A61B 18/1402 606/49 |
| 2016/0296219 | A1 | 10/2016 | Srivastava et al. |
| 2016/0303743 | A1 | 10/2016 | Rockrohr et al. |
| 2017/0165017 | A1 | 6/2017 | Chaplin et al. |

FOREIGN PATENT DOCUMENTS

| | | |
|---|---|---|
| DE | 19537320 A1 | 4/1997 |
| EP | 1151723 A2 | 11/2001 |
| JP | 2005218497 A | 8/2005 |
| JP | 2011509112 A | 3/2011 |
| JP | 2013-017542 A | 1/2013 |
| WO | WO-9114393 A1 | 10/1991 |
| WO | WO-2007088208 A1 | 8/2007 |
| WO | WO-2011002215 A2 | 1/2011 |
| WO | WO-2011161626 A2 | 12/2011 |
| WO | WO-2012005986 A1 | 1/2012 |
| WO | WO-2015023865 A1 | 2/2015 |
| WO | WO-2016025132 A1 | 2/2016 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. 14836179.3, dated May 30, 2017, 8 pages.
Article 94(3) Communication in EP Application No. 14836179.3, dated Jul. 26, 2019.
Office Action for JP Application No. 2019-198561, dated Nov. 17, 2020.
Office Action for KR Application No. 10-2016-7006620, dated Dec. 24, 2020.

* cited by examiner

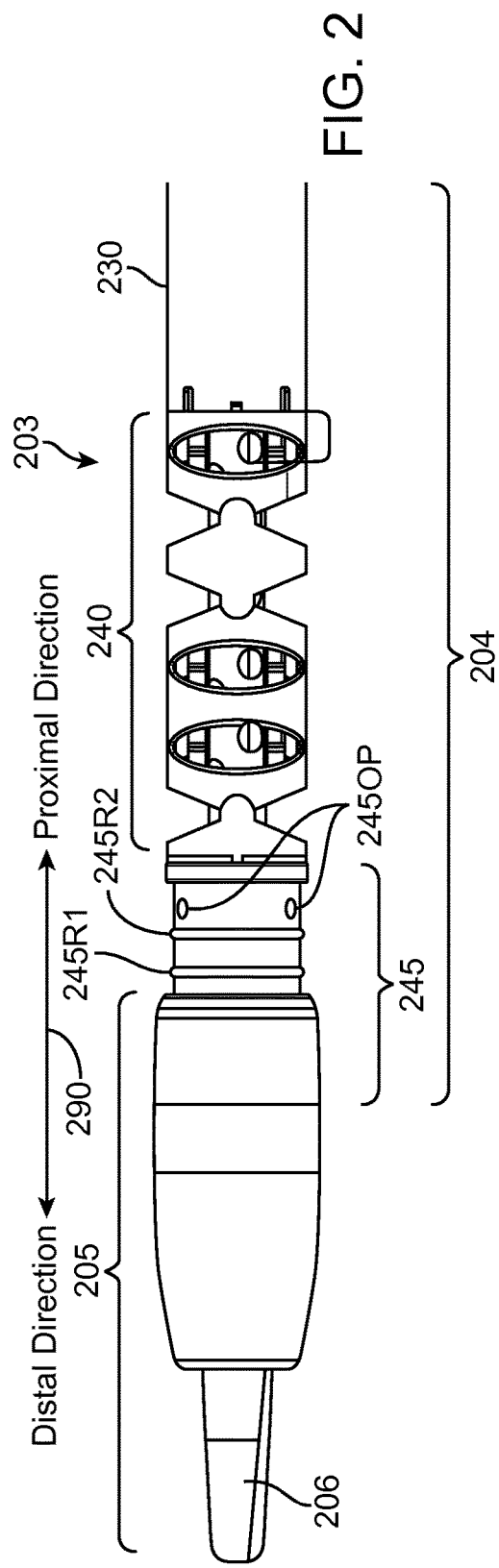
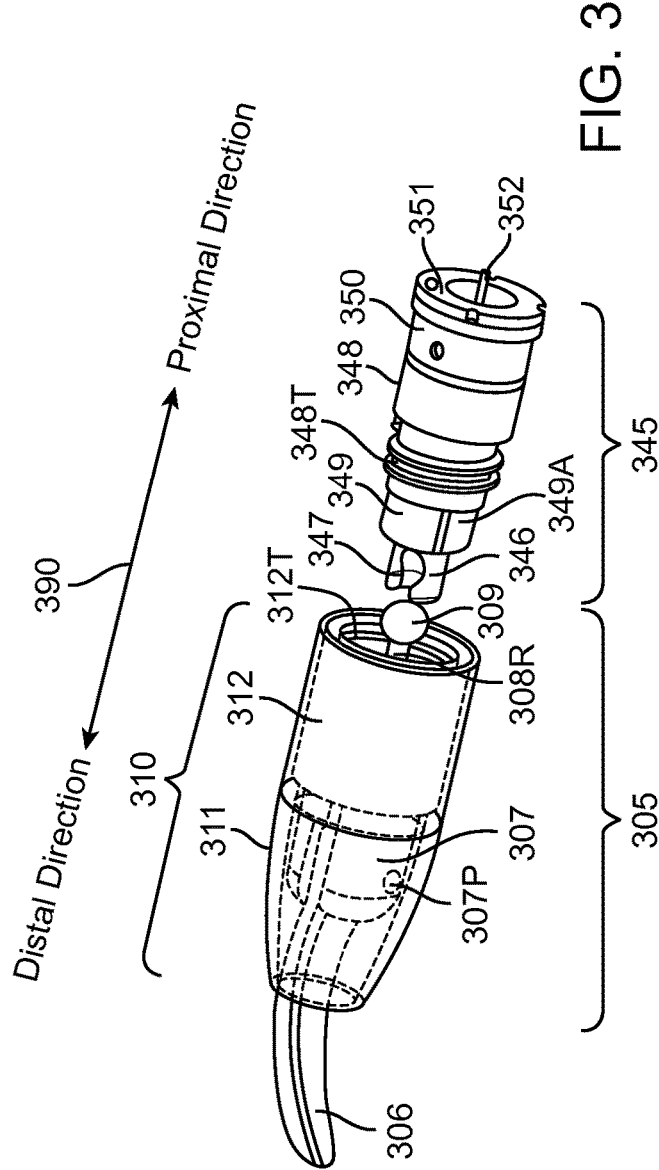

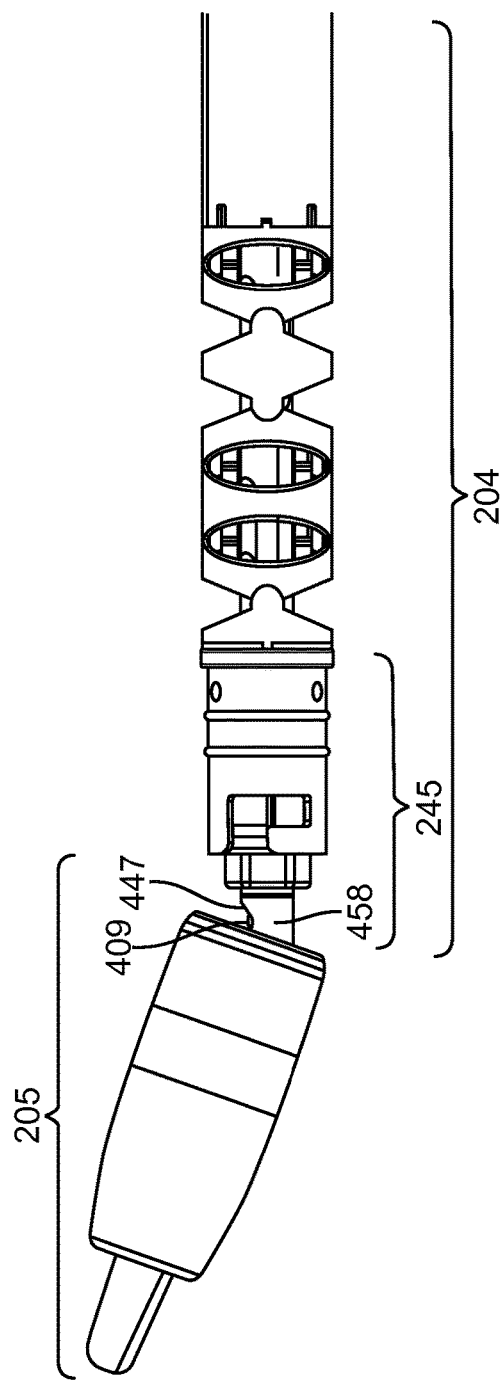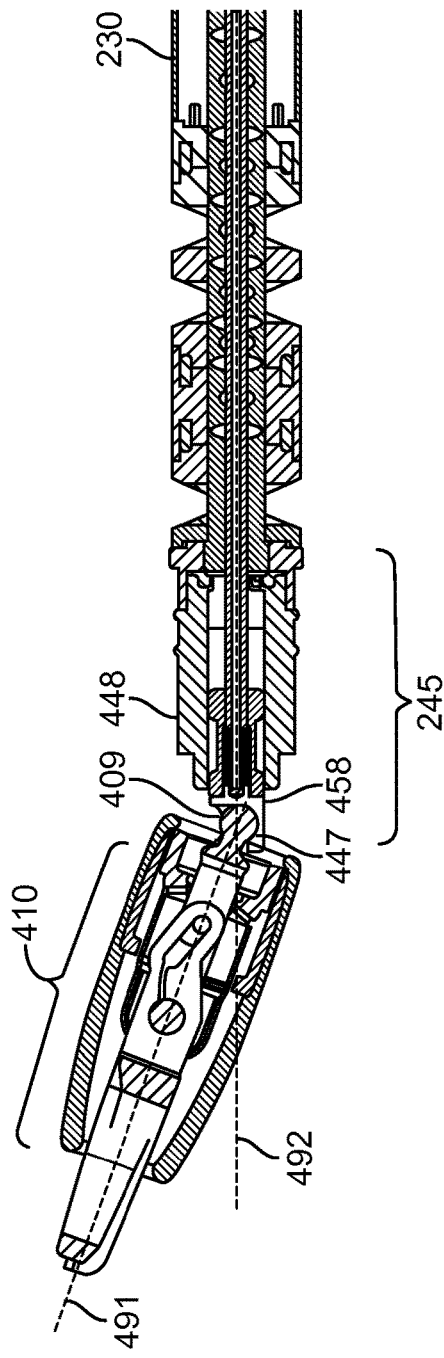

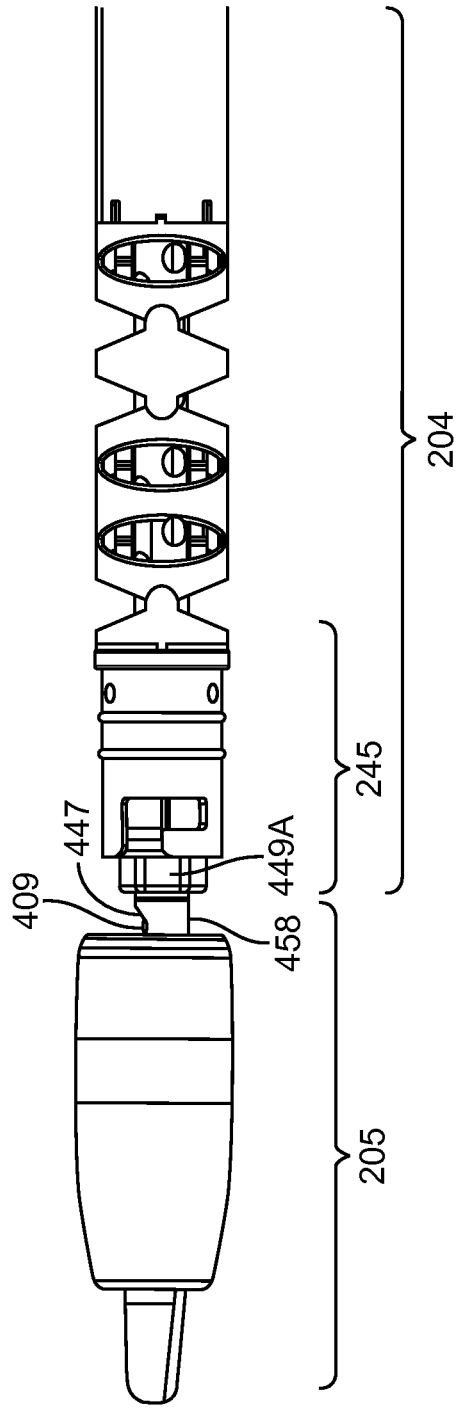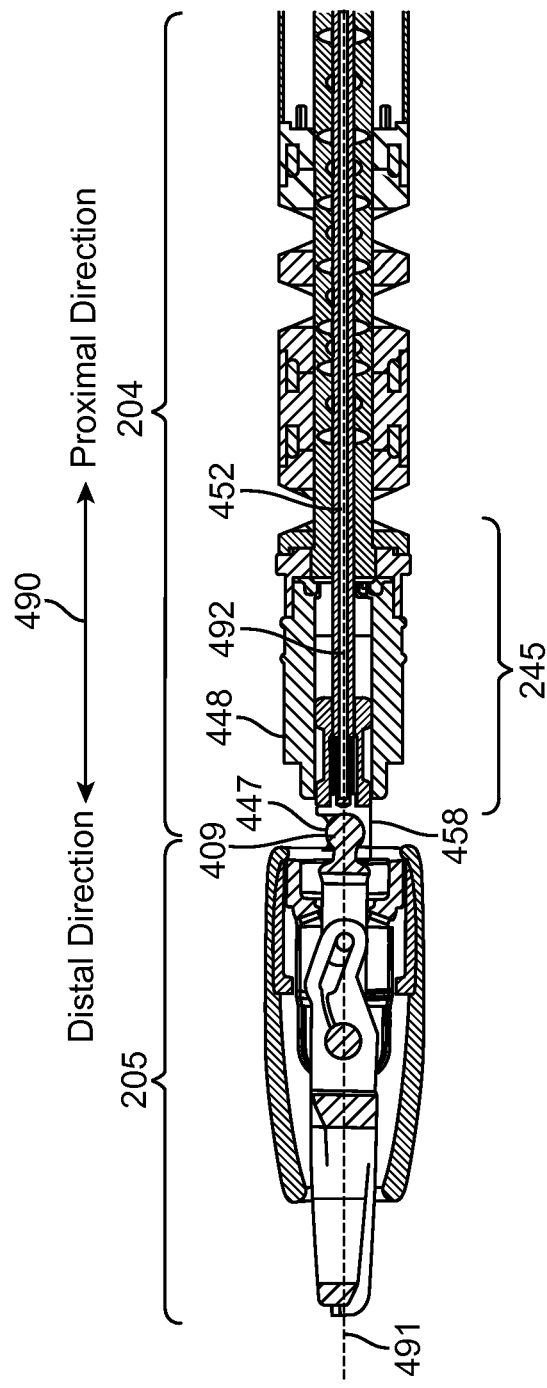

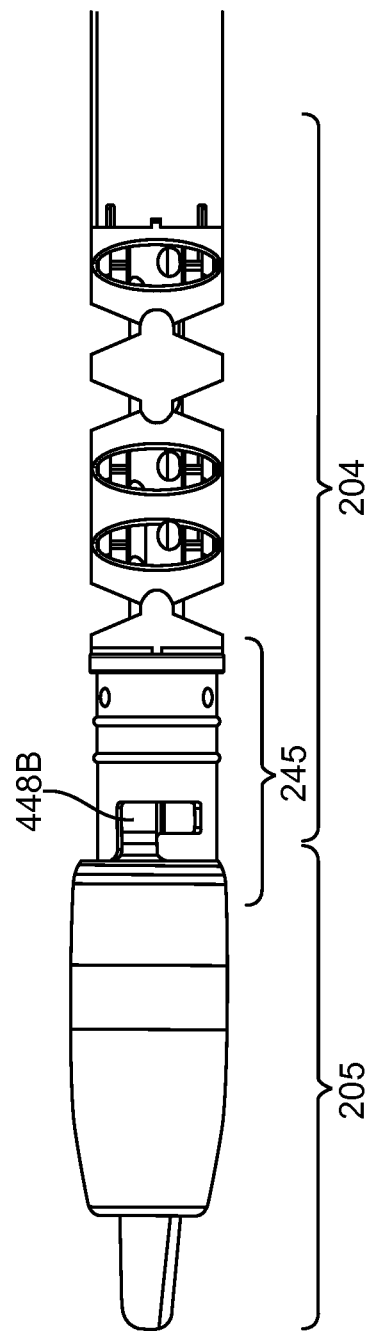
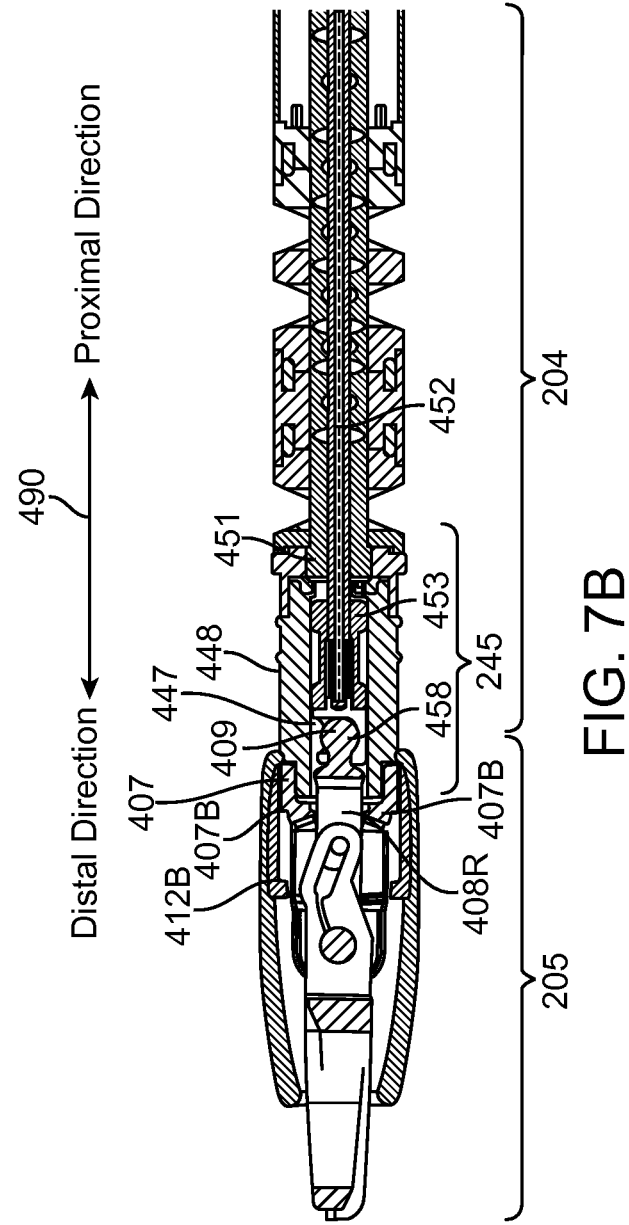
FIG. 7A
FIG. 7B

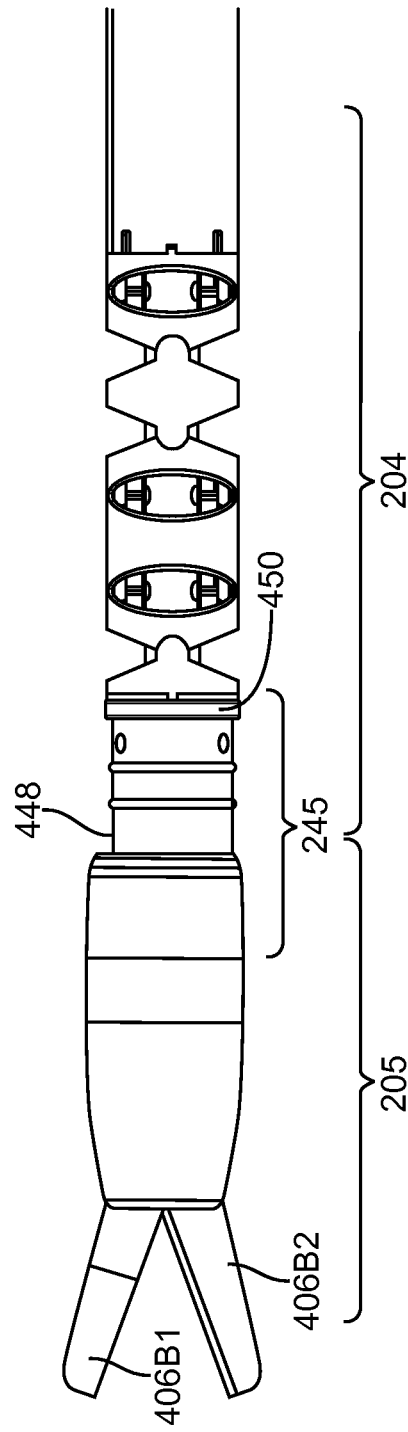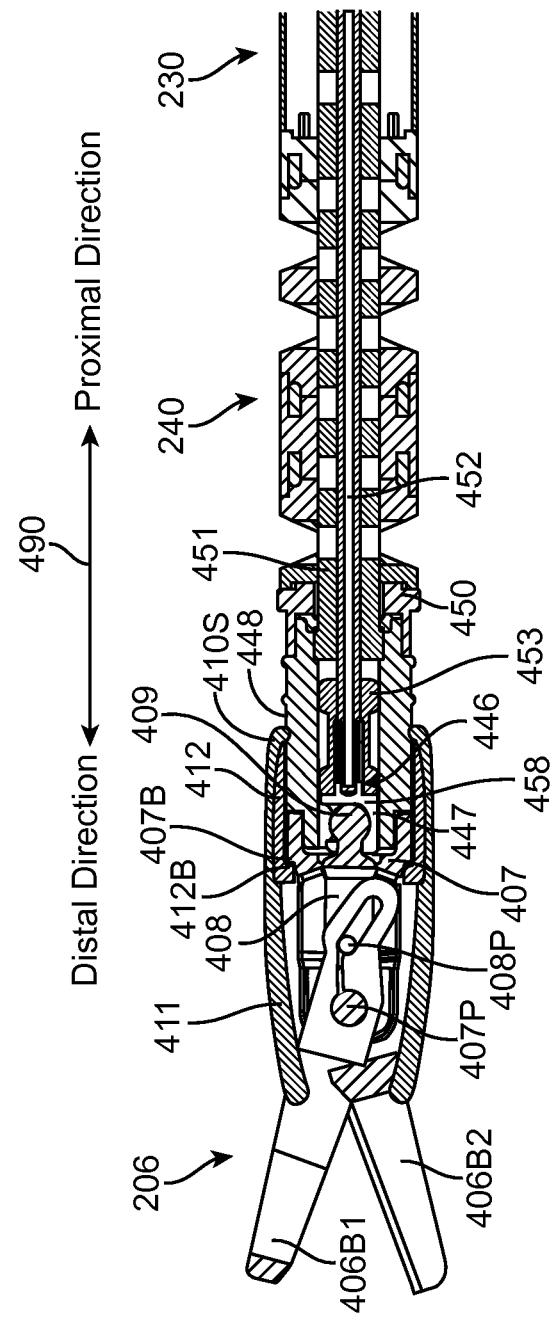

REUSABLE SURGICAL INSTRUMENT WITH SINGLE-USE TIP AND INTEGRATED TIP COVER

RELATED APPLICATIONS

This application is the U.S. national phase of International Application No. PCT/US2014/051098, filed Aug. 14, 2014, which designated the U.S. and which claims priority to and the benefit of:

U.S. Patent Application No. 61/866,127, (filed Aug. 15, 2013, disclosing "REUSABLE SURGICAL INSTRUMENT WITH SINGLE-USE TIP AND INTEGRATED TIP COVER," by William J. Park), each of which is incorporated herein by reference.

BACKGROUND

Field of the Invention

The present invention relates generally to surgical instruments, and more particularly to surgical instruments including reusable and disposable components.

Description of Related Art

Robotically controlled surgical instruments are often used in minimally invasive medical procedures. (As used herein, the terms "robot" or "robotically" and the like include teleoperation or telerobotic aspects.) The surgical instruments are wholly reusable or wholly disposable.

Such surgical instruments typically include an end effector. Examples of end effectors include a tool such as forceps, a cutting tool, or a cauterizing tool. An end effector assembly including the end effector typically is mounted on a wrist mechanism at the distal end of a main tube of the instrument.

During a medical procedure, the end effector assembly and the distal end of the main tube can be inserted directly or through a cannula into a small incision or a natural orifice of a patient to position the end effector at a surgical site within the patient. The wrist mechanism is used to position, orient, and move the end effector when performing the desired procedure at the surgical site. Tendons, e.g., cables or similar structures, extending through the main tube of the instrument typically connect the wrist mechanism to a transmission or backend mechanism that typically is motor driven in response to a doctor's instructions provided via a master control system. The reusable surgical instruments employed during minimally invasive medical procedures are generally complex mechanical devices having many separate components (e.g., cables and mechanical members).

SUMMARY

In one aspect, an apparatus includes a disposable surgical instrument tip assembly, sometimes referred to as a disposable tip assembly. The disposable tip assembly includes a locking tip cover, an end effector assembly, and an actuator rod assembly. The actuator rod assembly is coupled to the end effector assembly.

In one aspect, the combination of the end effector assembly and the actuator rod assembly is installed on a tip interface at a distal end of a reusable instrument portion. After the combination is installed, the locking tip cover is installed on the end effector assembly and locked to the tip interface. In another aspect, the locking tip cover is installed on the combination of the end effector assembly and the actuator rod assembly to form a single assembly. This single assembly is then installed on the tip interface at the distal end of the reusable instrument portion. Thus, in the first example, the locking tip cover is not preinstalled and in the second example, the locking tip cover is preinstalled.

The locking tip cover includes an external cover and a locking device. The external cover has a proximal end portion and a distal end. The locking device is mounted inside the proximal end portion of the external cover. The locking device has an inner wall that defines a central lumen.

The end effector assembly includes an end-effector body assembly and an end effector. The end effector is coupled to the end-effector body assembly. The end-effector body assembly is enclosed within the external cover, when the external cover is installed. When the external cover is first placed over the end-effector assembly, the end-effector body assembly is mounted in the central lumen of the locking device so that the locking device has two degrees of freedom relative to the end-effector body assembly.

The actuator rod assembly is connected to the end effector assembly. The actuator rod assembly includes a first quick connect/disconnect element at a proximal end of the actuator rod assembly.

In one aspect, the end effector is a blade set. In this aspect, the end-effector body assembly is a clevis. The blade set is monopolar-curved scissors, in one embodiment.

In another aspect, the apparatus includes a reusable surgical instrument. The reusable surgical instrument includes a distal end portion comprising a tip interface.

The tip interface includes an instrument tip and a grip actuator element. The instrument tip includes a distal end, a lock interface element, and a central lumen. The grip actuator element is positioned in the central lumen of the instrument tip. The grip actuator element includes a second quick connect/disconnect element. The second quick connect/disconnect element is configured to mate with the first quick connect/disconnect element. In one aspect, the first quick connect/disconnect element comprises a ball, and the second quick connect/disconnect element comprises a socket configured to receive the ball.

The reusable surgical instrument also includes a tendon having a first end coupled to the second quick connect/disconnect element. The reusable surgical instrument further includes a push-pull drive assembly coupled to a second end of the tendon. In a first state, the push-pull drive assembly applies a first force to the tendon to move the second quick connect/disconnect element to a first location. The first location is distal to the distal end of the instrument tip. In a second state, push-pull drive assembly applies a second force to the tendon to move the second quick connect/disconnect element from the first location to a second location. In the second location, the second quick connect/disconnect element is positioned within the central lumen of the instrument tip.

In one aspect, the tip interface further includes a seal mounted on a proximal end the instrument tip. In another aspect, the tip interface includes a seal mounted on an outer circumferential surface of the grip actuator element.

BRIEF DESCRIPTION OF THE DRAWINGS

FIG. 2 is an illustration of a first aspect of a reusable instrument portion and a disposable instrument tip assembly.

FIG. 3 is an illustration of a second aspect of a reusable instrument portion and a disposable instrument tip assembly.

FIG. 5A is an illustration of a second stage in attaching a disposable instrument tip assembly to a reusable instrument portion.

FIG. 5B is a cutaway view of the apparatus of FIG. 5A.

FIG. 6A is an illustration of a third stage in attaching a disposable instrument tip assembly to a reusable instrument portion.

FIG. 6B is a cutaway view of the apparatus of FIG. 6A.

FIG. 7A is an illustration of a fourth stage in attaching a disposable instrument tip assembly to a reusable instrument portion.

FIG. 7B is a cutaway view of the apparatus of FIG. 7A.

FIG. 9A is an illustration the configuration of a disposable instrument tip assembly and a reusable instrument portion during use.

FIG. 9B is a cutaway view of the apparatus of FIG. 9A.

Figure 1:
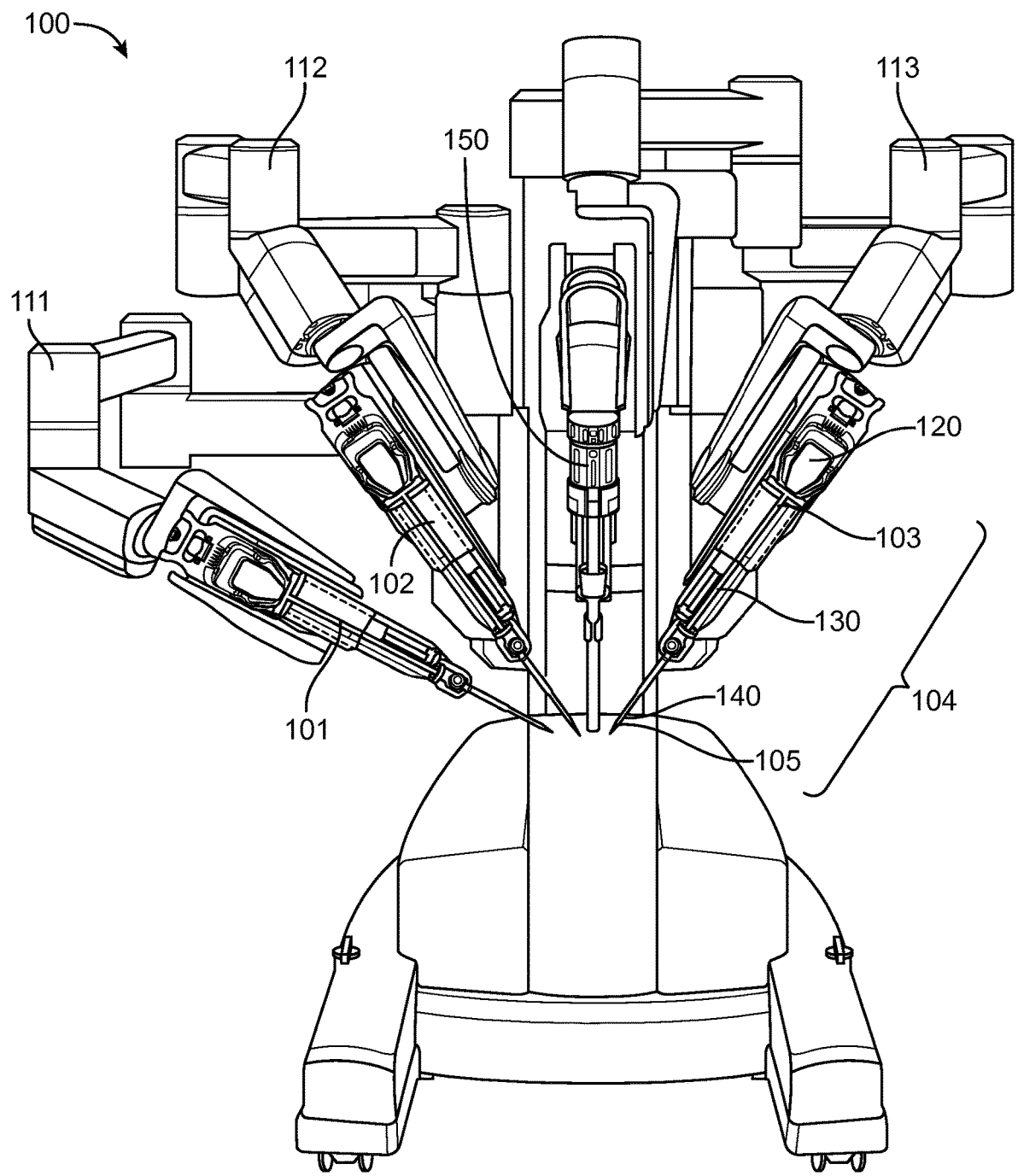
FIG. 1 is an illustration of a surgical system that includes a surgical instrument with a reusable instrument portion and a disposable instrument tip assembly.

In the drawings, for single digit figure numbers, the first digit in the reference numeral of an element is the number of the figure in which that element first appears. For double-digit figure numbers, the first two digits in the reference numeral of an element is the number of the figure in which that element first appears.

DETAILED DESCRIPTION

In accordance with an aspect of the invention, a surgical system 100 (FIG. 1) includes a plurality of surgical instruments 101, 102, 103. Surgical instrument 103 includes a reusable instrument portion 104 and a disposable surgical instrument tip assembly 105, sometimes referred to as disposable tip assembly 105. Disposable tip assembly 105 includes an end effector assembly that in turn includes an end effector such as a clamp, a grasper, scissors, a clip applier, or a needle holder.

In one aspect, disposable tip assembly 105 includes a locking tip cover that locks disposable tip assembly 105 to reusable instrument portion 104. In. FIG. 1, disposable tip assembly 105 is mounted on and locked to a tip interface at a distal end of reusable instrument portion 104. In FIG. 1, the distal direction is towards the end of a surgical instrument where disposable tip assembly 105 is mounted and the proximal direction is towards backend mechanism 120.

To facilitate mounting disposable tip assembly 105 on the tip interface of reusable instrument portion 104, disposable tip assembly 105 includes a first quick connect/disconnect element and the tip interface includes a second quick connect/disconnect element. The second quick connect/disconnect element is coupled to a tendon. The tendon is also coupled to an actuator assembly that provides forces that push and pull (push/pull) the tendon.

As explained more completely below, the tendon pushes second quick connect/disconnect element beyond the distal end of the tip interface. The first quick connect/disconnect element is coupled to, e.g., mated with the exposed second connect/disconnect element. Then, the tendon pulls the mated pair of elements into a channel, sometimes referred to as a central lumen, in the tip interface.

Next, the locking tip cover is moved proximally until a stop is reached and then the locking tip cover is locked to the tip interface, e.g., the tip cover is rotated with respect to the tip interface. In one aspect, the locking tip cover includes two parts, an external cover and a locking device. The locking device is positioned within a proximal portion of the external cover.

In one aspect, the combination of the end effector assembly and the actuator rod assembly is installed on the tip interface at a distal end of a reusable instrument portion. After the combination is installed, the locking tip cover is installed on the end effector assembly and locked to the tip interface. In another aspect, the locking tip cover is installed on the combination of end effector assembly and the actuator rod assembly to form a single assembly. This single assembly is then installed on the tip interface at the distal end of the reusable instrument portion. Thus, in the first example, the locking tip cover is not preinstalled and in the second example, the locking tip cover is preinstalled.

In another aspect, the locking tip cover is a single component. For example, the external cover is not used and so the locking tip cover is the locking device. As described below, the external cover provides electrical isolation in one aspect. If the electrical isolation is not needed, only the locking device could be used as the locking tip cover. In another example, the locking tip cover is a single integral component—a one-piece component—that provides both the external cover functionality and the locking device functionality.

An end effector assembly includes an end-effector body assembly and an end effector. The end effector is coupled to the end-effector body assembly. The end-effector body assembly is enclosed within the external cover. The end-effector body assembly is mounted in a central lumen of the locking device so that the locking device has two degrees of freedom relative to the end-effector body assembly.

The disposable tip assembly also includes an actuator rod assembly connected to the end effector assembly. The actuator rod assembly includes the first quick connect/disconnect element at a proximal end of the actuator rod assembly.

The mating of the first quick connect/disconnect element of disposable tip assembly 105 with the second quick connect/disconnect element of the tip interface establishes a mechanical connection between the end effector and an actuator drive assembly. The actuator drive assembly generates forces that push/pull the tendon connected to the second quick connect/disconnect element. Also, in aspects where a voltage is applied to the end effector, the mated quick connect/disconnect elements provide an electrical path between the end effector and a supply voltage.

The external cover of disposable tip assembly 105 combined with an internal seal seals any fluids that enter the assembly within the assembly. This prevents a fluid path from an electrically energized portion of disposable tip assembly 105 from reaching the patient along an unintended route and prevents the fluids from reaching other parts of the surgical instrument. Also, the external cover provides electrical isolation, for the portions of the assembly not intended to supply energy, when a voltage is applied to the end effector.

A wholly reusable surgical instrument with monopolar-curved scissors is one of the most highly utilized robotic surgical instrument types. A voltage is applied to the curved scissors.

Unfortunately, the cutting performance of reusable monopolar-curved scissors is not as good as single-use laparoscopic instruments, primarily because the current density through the sharp blade edge dulls the blade. As a result, the sharpness of the blade declines over the life of the reusable instrument. The maximum life of the reusable instrument can be driven by the ability to maintain a sharp blade.

In one aspect, a surgical instrument 103 includes a disposable tip assembly 105 that in turn includes a disposable blade set. In one aspect, disposable tip assembly 105 is used for a single procedure and then disposed, e.g., assembly 105 is a single use disposable tip assembly.

However, in some situations, the disposable blade set may perform satisfactorily for more than a single procedure. In such situations, disposable tip assembly 105 may be used for more than one procedure if after each procedure the tip assembly is properly cleaned and sterilized. When disposable tip assembly 105 is used for more than one procedure, a new tip cover is used in each procedure. In this multi-use application, disposable tip assembly 105 is used until performance of the blade set is unsatisfactory to the surgeon and then is removed from reusable surgical instrument portion 104 and discarded.

Disposable tip assembly 105 not only provides the user with sharp blades, but also extends the life of reusable instrument portion 104. No longer must the reusable part of surgical instrument 103 be discarded when the blade set becomes dull. Thus, the use of disposable tip assembly 105 may reduce the cost per procedure for surgical instrument 103 because portion 104 can be used in more procedures than the equivalent wholly reusable surgical instrument. The incremental cost of disposable tip assembly 105 may be offset by the extended life of reusable instrument portion 104.

As described more completely below, disposable tip assembly 105 with a disposable blade set is quickly and easily installed on and uninstalled from reusable instrument portion 104 using the quick connect/disconnect elements. The quick connection and disconnection enables efficient user workflow independent of whether the locking tip cover is preinstalled.

Also as described more completely below, an integrated tip cover fastens disposable tip assembly 105 onto reusable instrument portion 104 and ensures that cautery energy is only applied by the intended portions of the blades. This also simplifies the user workflow and reduces cost by minimizing the number of components in disposable tip assembly 105. This advantage is applicable independent of whether the locking tip cover is preinstalled.

In one aspect, system 100 is the da Vinci® Surgical System commercialized by Intuitive Surgical, Inc. Each surgical instrument in the plurality of surgical instruments 101, 102, and 103 is mounted on a docking port on a manipulator arm 111, 112, and 113, respectively. The docking ports of system 100 generally include drive motors that provide mechanical power for operation of instruments 101, 102, 103. These drive motors are sometimes referred to as an actuator drive assembly. Each docking port may additionally each include an electrical interface for communication with the instrument mounted on that docketing port.

System 100 is illustrative only and is not intended to be limiting to this specific implementation. For example, disposable tip assembly 105 can also be used on surgical instruments in a teleoperated surgical system with a single entry port, which has a system configuration different from that illustrated in FIG. 1.

Using surgical instrument 103 as an example, reusable instrument portion 104 includes a transmission or backend mechanism 120, a main tube 130 extending from the backend mechanism 120, and a wrist mechanism 140 at the distal end of main tube 130. Disposable tip assembly 105 is coupled to wrist mechanism 140.

Surgical instrument 103 is also illustrative and is not intended to be limiting. For example, a parallel motion mechanism could be included between the distal end of main tube 130 and wrist mechanism 140.

Drive cables or tendons and electrical conductors that are connected to wrist mechanism 140 extend through main tube 130 and connect to backend mechanism 120. Backend mechanism 120 typically provides a mechanical coupling of the drive tendons to drive motors in system 100. System 100 can thus control movement and tension in the tendons as needed to move or position wrist mechanism 140 and to operate an end effector in disposable tip assembly 105.

In the example of FIG. 1, a camera system 150 is similarly mounted on a manipulator arm of system 100. The views from camera system 150, which may be stereoscopic or three-dimensional, are viewed at a master control console (not shown). A processing system of system 100 provides a user interface enabling a doctor or other medical personnel to see and manipulate camera system 150 and instruments 101, 102, and 103.

For example, an arm 113 can be used to insert the end of surgical instrument 103 through a cannula in a small incision in a patient undergoing a medical procedure. Alternatively, in a single port system, surgical instrument 103 is inserted through a channel in an entry guide mounted in a cannula. Backend mechanism 120 is used to operate wrist mechanism 140 and the end effector at the surgical site inside the patient. The diameter or diameters of main tube 130, wrist mechanism 140, and disposable tip assembly 105 are generally selected according to the size of the cannula with which instrument 103 is used, and in an exemplary embodiment, wrist mechanism 140 and main tube 130 are about 4 mm, 5 mm, or 8 mm in diameter to match the sizes of some existing cannula systems.

FIG. 2 illustrates in more detail one aspect of a distal end of a reusable surgical instrument 203 that includes a reusable instrument portion 204 and a disposable tip assembly 205 affixed to portion 204. Reusable instrument portion 204 includes a main tube 230 having a distal end coupled to a wrist 240. The distal end of wrist 240 is coupled to a tip interface 245. Arrow 290 shows the proximal direction and the distal direction with respect to reusable surgical instrument 203.

Disposable tip assembly 205 is mounted on and connected to tip interface 245, e.g., affixed to reusable instrument portion 204 in this aspect. Disposable tip assembly 205 includes a disposable blade assembly 206. Use of a blade assembly with blades as the end effector is illustrative only and is not intended to be limiting to this specific end effector. In view of this disclosure, one knowledgeable in the field can implement an end effector assembly of the person's choice in the disposable tip assembly described herein.

Only a part of tip interface 245 is visible in FIG. 2. The remainder of tip interface 245 is contained within disposable tip assembly 205.

In one aspect, disposable tip assembly 205 is a single use assembly. However, as described above for disposable tip assembly 105 in other aspects, disposable tip assembly 205 may be used in a limited number of surgical procedures, i.e., until the performance of the element is unsatisfactory, and then discarded. In the multiple use aspect of disposable tip assembly 205, a new tip cover is used in each surgical procedure and the other parts of disposable tip assembly 205 are properly cleaned and sterilized. Independent of whether disposable tip assembly 205 is used in a single surgical procedure or in a few surgical procedures, the lifetime of disposable tip assembly 205 is less than the lifetime of the wrist and shaft, for example, of the surgical instrument and so is disposable relative to the surgical instrument.

Tip interface 245 and disposable tip assembly 205 are designed to minimize the longitudinal length distal to the last joint in wrist 240. In addition, as explained more completely below, tip interface 245 and disposable tip assembly 205 are designed to permit easy connection and disconnection of tip interface 245 to disposable tip assembly 205. In addition, the combination of tip interface 245 and disposable tip assembly 205 provides electrical isolation for any voltage that is applied to a blade in disposable blade assembly 206. This combination of tip interface 245 and disposable tip assembly 205 also seals any electrically energized fluid created by such a voltage within the combination so that the electrically "hot" fluid does not contact the patient in an unintended manner and does not flow proximally into reusable instrument portion 204.

Disposable tip assembly 205 makes at least a mechanical connection to surgical instrument 203 via tip interface 245. In some aspects, an electrical connection is also made. A first mechanical connection is made between a mechanical actuator rod assembly in disposable tip assembly 205 and a grip actuator element in tip interface 245. When the mechanical connection is made, in one aspect, an electrical connection also is established between a blade in blade assembly 206 and a electrical connector in the backend mechanism of surgical instrument 203 so that a voltage can be applied to the blade, e.g., about 3000 volts. Finally, a lockable mechanical connection locks disposable tip assembly 205 to tip interface 245 so that disposable tip assembly 205 is affixed to tip interface 245.

In one aspect, the lockable mechanical connection is a partial rotation connection, e.g., disposable tip assembly is mounted on tip interface 245 and then rotated a quarter of a turn to lock disposable tip assembly 205 to tip interface 245. An example of such a partial rotation connection is a bayonet connection. In another aspect, the lockable mechanical connection is implemented using threads on disposable tip assembly 205 and tip interface 245. The mechanical connection is referred to as lockable, because when disposable tip assembly 205 is affixed to tip interface 245, blade assembly 206 is locked in place and is ready for use.

In FIG. 2, at the proximal end of tip interface 245 are two ribs 245R1, 245R2 that extend radially outward from the outer surface of tip interface 245. Ribs 245R1, 245R2 are optional. When a sheath is used over wrist mechanism 240, the distal end of the sheath forms a seal with ribs 245R1, 245R2. Also, in one aspect, pins are inserted through two openings 245OP in the proximal end of tip interface 245 in attaching wrist mechanism 240 to tip interface 245.

FIG. 3 illustrates another aspect of a disposable tip assembly 305 that is configured to be mounted on and connected to a tip interface 345. Tip interface 345 is connectable to a wrist or other element of a reusable surgical instrument such as that shown in FIGS. 1 and 2. Arrow 390 shows the proximal direction and the distal direction with respect to disposable tip assembly 305.

Disposable tip assembly 305 includes a disposable blade assembly 306, a locking tip cover 310, and an actuator rod assembly 308 (see FIGS. 10A to 10D). As explained more completely below, disposable blade assembly 306 includes a pair of blades, a clevis 307, and a pin 307P.

Also, as explained more completely below, in one aspect locking tip cover 310 includes two parts, an external cover 311 and a locking device 312. In FIG. 3, external cover 311 has been made transparent to permit viewing the parts contained within external cover 311. This for ease of illustration only and is not intended to imply that external cover 311 is or must be transparent.

In this aspect, locking device 312 has a cylindrical outer surface and threads 312T formed in inner proximal surface. In one aspect, locking device 312 is a nut that is free to rotate on clevis 307. Locking device 312 is made from a non-electrically conductive rigid material.

External cover 311 is made from a non-conductive flexible material, like silicone or a flexible, medical grade thermoplastic elastomer. An example of a thermoplastic elastomer is Pellethane® polyurethane thermoplastic elastomer provided by The Upjohn Company. (Pellethane® is a U.S. registered trademark of The Upjohn Company of Kalamazoo, Mich.).

The non-conductive flexible material is either overmolded or bonded into place, and the non-conductive flexible material acts as an insulation barrier covering portions of an active electrode not intended for patient contact. This material is flexible to allow for opening and closing of the blades. The proximal end of external cover 311 also has a feature that acts as a fluid seal, preventing electrically hot fluids from contacting the patient in an unintended location.

The mechanical actuation of disposable blade assembly 306 is provided through a ball and socket interface, which is an example of a quick connect/disconnect interface. A ball 309 on the proximal end of actuator rod 308R fits into a socket 347 that is located at the distal end of a grip actuator element 346. Ball 309 and socket 347 are examples of a first quick connect/disconnect element and a second quick connect/disconnect element, respectively. The use of ball 309 and socket 347 is illustrative only and is not intended to be limiting. In view of this disclosure, one knowledgeable in the field can implement a quick connect/disconnect interface with two elements that provide the connect/disconnect functionality described herein while preserving the other features associated with quick connect/disconnect interface, e.g., a cylinder with filleted edges.

One aspect of the connect/disconnect interface is that the interface has a rotational degree of freedom, e.g., ball 309 can rotated in socket 347. As main tube 230 is rolled, the tendon connected to the connect/disconnect interface is fixed at the proximal end. The rotational degree of freedom of the connect/disconnect interface allows reduction of the torsional stiffness of the tendon compared to a tendon connected to an interface that did not have a rotational degree of freedom.

Grip actuator element 346 is positioned in and slides longitudinally in a lumen of instrument tip 348 and is coupled to a tendon 352. A wrist-disposable tip adapter 350 is affixed to the proximal end of instrument tip 348. A seal (not visible in FIG. 3) is positioned between the proximal end of instrument tip 348 and wrist-disposable tip adapter 350. The seal isolates the wrist and main tube from electrically "hot" fluid that might otherwise pass through disposable tip assembly 305 into a central lumen of instrument tip 348. Tendon 352 passes through a guide (not shown) that is mounted in a central lumen at the proximal end of wrist-disposable tip adapter 350. In one aspect, the guide is implemented as a flexible bushing. Tendon 352 passes through a wrist and so is flexible.

The distal end of instrument tip 348 includes an orientation alignment feature, in this example, a flat surface 349A. A corresponding orientation alignment feature is provided in the proximal end of clevis 307. The two orientation alignment features mate such that when instrument tip 348 is affixed to disposable tip assembly 305, disposable tip assembly 305 is properly oriented on the reusable surgical instrument portion.

The use of a single flat surface is illustrative only and is not intended to be limiting. In another aspect two opposed flat surfaces are used as the orientation alignment features. The particular alignment features used depends on the characteristics of the end effector of the disposable tip. For monopolar-curved shears, a single flat surface is used, because the end effector is asymmetric and needs to be installed in a unique orientation. If the end effector could be installed in one of two orientations, two opposed flat surfaces could be used as the orientation alignment features. In view of this disclosure, those knowledgeable in the field can use any orientation alignment features that provide the functionality described herein with respect to the orientation alignment features.

Instrument tip 348 also has a lock interface element, e.g., threads 348T on the outer surface that mate with threads 312T. The threads are used to lock disposable tip assembly 305 to tip interface 345.

FIGS. 4A, 5A, 6A, 7A, and 9A illustrate connecting disposable tip assembly 205 to reusable instrument portion 204. FIGS. 4B, 5B, 6B, 7B, 8, and 9B are cross-sectional drawings of the elements in FIGS. 4A, 5A, 6A, 7A, 2, and 9A, respectively.

Figure 4A:
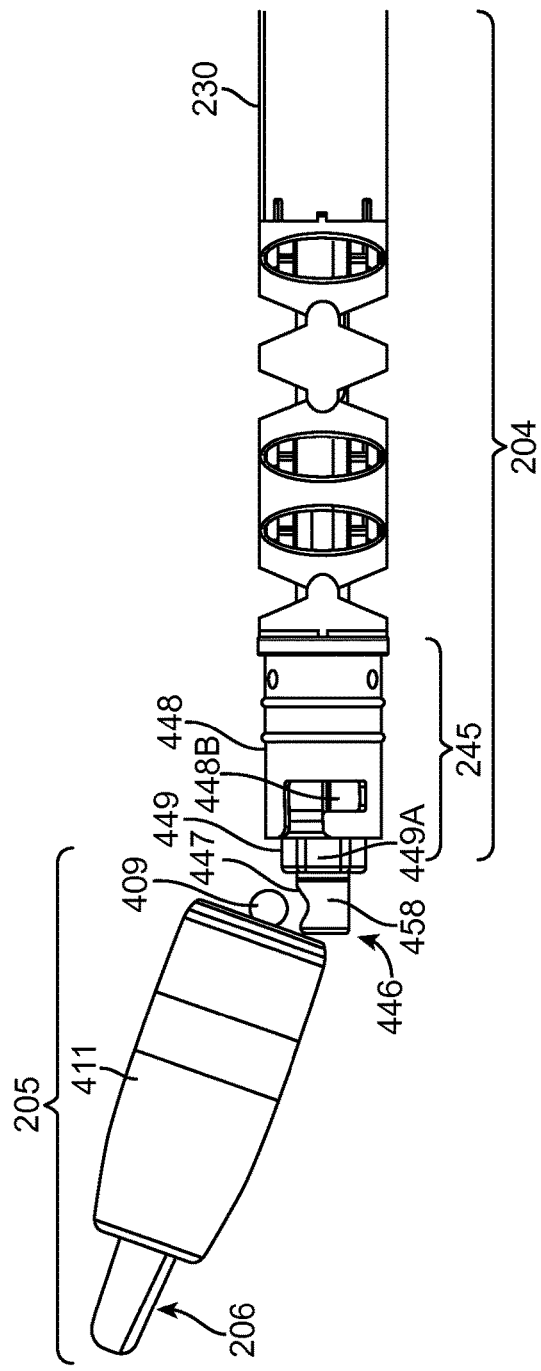
FIG. 4A is an illustration of the initial step in attaching a disposable instrument tip assembly to a reusable instrument portion.
Figure 4B:
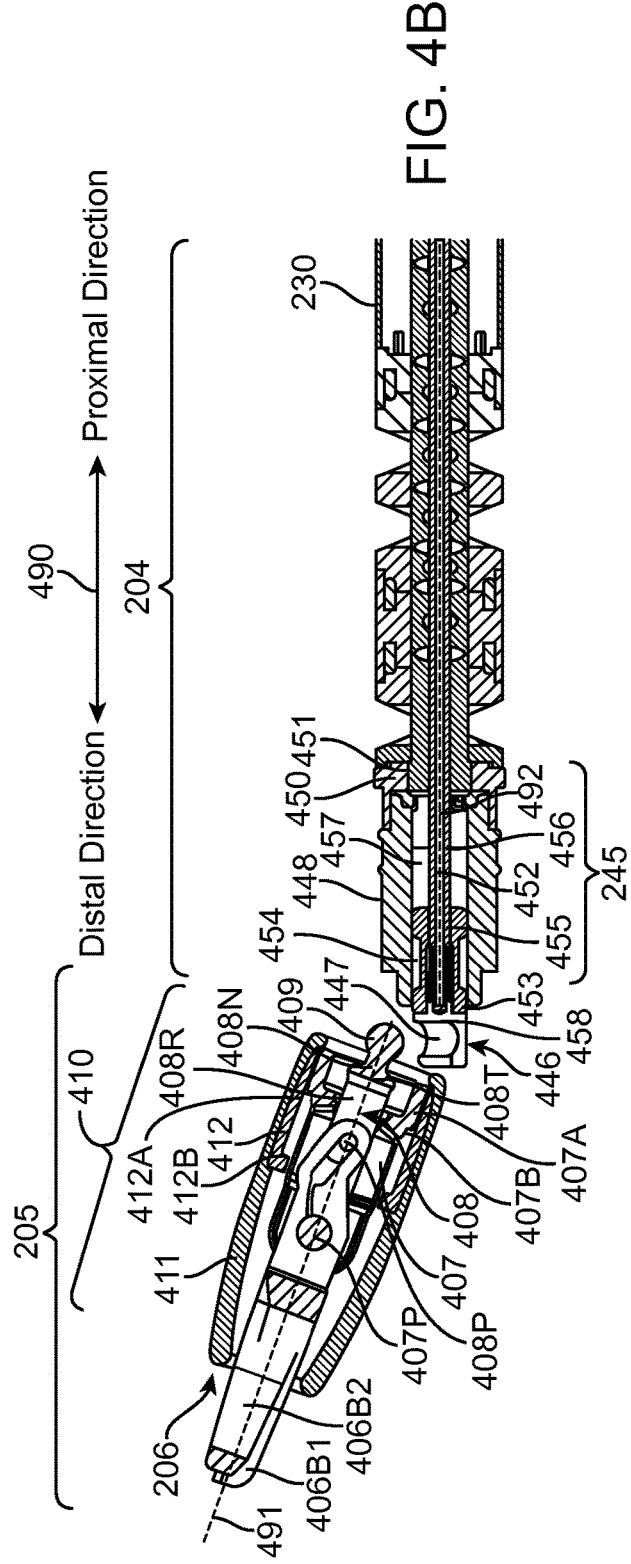
FIG. 4B is a cutaway view of the apparatus of FIG. 4A.

In FIG. 4A, disposable tip assembly 205 is positioned for connection to reusable instrument portion 204. FIG. 4B is the corresponding cross-sectional view. Grip actuator element 446 has been pushed out of a lumen 457 in instrument tip 448 so that socket 447 is positioned distally of the distal end of instrument tip 448. In FIGS. 4A and 4B, the distal direction is towards the tips of blades 406B1 and 406B2 in disposable blade assembly 206 and the proximal direction is towards the backend mechanism of surgical instrument 203 as show by arrow 490. In one aspect, grip actuator element 446 is moved about 0.18 inches (4.5 mm) from a normal closed position of grip actuator element 446 (see FIGS. 2 and 8) to receive ball 409 of disposable tip assembly 205.

A shown in FIG. 4B, disposable blade assembly 206 includes two blades 406B1 and 406B2 that are connected to clevis 407 by a first pin 407P. A second pin 408P of actuator rod assembly 408 is positioned in a slot in the proximal ends of blades 406B1 and 406B2. Pin 408P is moved in the slot to actuate the blades. In one aspect, second pin 408P passes through and floats in a distal end of a solid cylindrical rod 408R in actuator rod assembly 408.

In one aspect, blades 406B1 and 406B2 are monopolar-curved blades that are made of 17-4 PH stainless steel conditioned to H900, which is referred to herein as 17-4 stainless steel. In one aspect, blades 406B1 and 406B2 are formed using electrical discharge machining (EDM). In another aspect, blades 406B1 and 406B2 are stamped out of 301 stainless steel.

Blades 406B1 and 406B2 are thin, e.g., have thicknesses of about 0.020 inches (0.5 mm). The cutting surface of blades 406B1 and 406B2 has a length of about 0.35 inches (8.9 mm) exposed cutting surface when open in one aspect. In this aspect, the length of the blade from the distal end to clevis pin 407P is about 0.50 inches (12.7 mm). Blades 406B1 and 406B2 are slightly curved and are flexed to provide bias. In one aspect, the radius of the blade curve is about 0.35 inches (8.9 mm).

The blades would normally interfere with one another but to assemble the blades, the blades have to deflect. The force required to deflect the blades is what produces the bias force between the blades, in one aspect. This force is a function of the blade geometry (curve), the blade thickness, and the gap between the arms of clevis 407 and the blade stack that is established during the swaging process. This bias eliminates the need for a bias spring that is typically found in surgical scissors. However, in some aspects, the biasing could be provided by biasing springs such as Belleville washers.

Clevis 407 can be made of one an electrically non-conducting material and an electrically conducting material. An electrically non-conducing material suitable for clevis 407, for example, is made of glass-filled polyphthalamide (PPA). The glass-filled material has adequate strength, biocompatibility, sterilization compatibility, and PPA has very good arc tracking resistance, which is an advantage in high voltage monopolar cautery. A suitable PPA is available from Solvay Plastics under Amodel® PPA A-1133 HS. (Amodel® is a U.S. registered trademark of Solvay Advanced Polymers, L.L.C. of Alpharetta, Ga.) An electrically non-conducting clevis 407 lengthens any possible unintended arc path from blades 406B 1 and 406B2 and/or actuator rod assembly 408 to the patient and/or the body of the instrument when a voltage is applied to blades 406B 1 and 406B2.

However, in some aspects, clevis 407 can be made from an electrically conducting material. An electrically conducting clevis 407, for example, is made of stainless steel. In one aspect, 17-4 stainless steel is used. However, any stainless steel that can be used in metal injection modeling could be used.

In one aspect, actuator rod assembly 408 is made of 17-4 stainless steel and includes a solid cylindrical rod 408R with ball 409 at the proximal end of cylindrical rod 408R. In one aspect, the overall length of actuator rod assembly 408 is 0.28 inches (7.1 mm). The diameter of cylindrical rod 408R is 0.090 inches (2.28 mm) and the length is 0.28 inches (7.1 mm). In one aspect, ball 409 has a diameter of 0.70 inches (17.8 mm). Also, in one aspect, the backside of ball 409—the proximal side—has a small flat region to aid in manufacturing of the part. There is a transition region 408T between neck region 408N and ball 409. Transition region 408T reduces the diameter to the diameter of cylindrical rod 408R.

Locking tip cover 410 provides an electrically insulating seal component between the electrically hot active components of disposable tip assembly 205 and unintended contact with the patient. The electrically insulating seal component includes a rigid, non-conductive component, i.e., locking device 412, which locates disposable tip assembly 205 within instrument tip 448 and an overmolded seal, e.g., external cover 411. This seal also provide an isolation barrier component for fluids that enter disposable tip assembly 205.

In one aspect, locking device 412 is molded using an amorphous thermoplastic polyetherimide (PEI) material. An example of an amorphous thermoplastic PEI material is ULTEM® amorphous thermoplastic PEI material manufactured by Saudi Basic Industries Corporation (SABIC). (ULTEM® is a U.S. registered trademark of SABIC Innovative Plastics, Inc. besloten vennootschap (b.v.) NETHERLANDS Plasticslaan 1 Bergen op Zoom NETHERLANDS 4612PX.) In another aspect, locking device 412 is molded using a glass-filled polyphthalamide (PPA) such as that described above.

In one aspect, external cover 411 is made of a silicone rubber with high tear strength, e.g., a tear-resistant silicone elastomer. The silicone rubber is biocompatible and withstands at least 4 kV. Additionally, the high temperature resistance of silicone is advantageous with respect to the any heat that might be generated as energy is applied to the blades. An example of such a silicone rubber is sold by Dow Corning Corporation as Silastic® Biomedical Grade ETR Elastomer Q7-4750. (Silastic® is a U.S. registered trademark of Dow Corning Corporation of Midland, Mich.) Other suitable materials include flexible, medical grade elastomers including polyurethane thermoplastic elastomers such as Pellethane® polyurethane thermoplastic elastomer provided by The Upjohn Company. Any materials and any dimensions provided herein are illustrative only and are not intended to be limiting to those specific dimensions and materials.

Disposable tip assembly 205 has a longitudinal axis 491. Locking device 412 is free to rotate around longitudinal axis 491 and so free to rotate around clevis 407. Locking device 412 has a circumferential interior surface 412A that is flat in the cross-sectional view of FIG. 4B and extends distally from a proximal end of locking device 412 to a shoulder 412B formed perpendicular to interior surface 412A in this aspect.

A length of interior surface 412A substantially parallel to longitudinal axis 491 is selected based on at least two criteria. First, the length of interior surface 412A is such that when locking tip cover 410 is moved distally so that a proximal stop is encountered ball 409 extends beyond external cover 411 as shown in FIGS. 4A and 4B. In one aspect, male bayonet elements (see elements 712 in FIG. 7D) extending from circumferential interior surface 412A interfere with a surface on clevis 407 such that locking tip cover 410 is captive. Second, when disposable tip assembly 205 is moved proximally so that assembly 205 is mounted on and affixed to reusable surgical instrument portion 204, as described below, the length is such that shoulder 407B at the distal edge of surface 407A abuts shoulder 412B (see FIG. 8).

It should be understood that the features of surface 412A and shoulder 412B shown in FIG. 4B are illustrative only and are not intended to be limiting. In general, inner surface 412A and shoulder 412B of locking device 412 are selected to work with outer surface 407A and shoulder 407B of clevis 407 to provide the functionally just described. In general, shoulders on both locking device 412 and clevis 407 are designed to lock clevis 407 in places as the two components are drawn together and locking device 412 is actuated.

Locking device 412 includes two protrusions 712 (FIG. 7D) extending radially inward from interior surface 421A that are used to lock to disposable tip assembly 205 to instrument tip 448 through the use of a bayonet fixture or a one quarter turn type feature as described more completely below. The use of a one quarter turn locking mechanism allows the length of surface 412A to be minimized relative to a threaded connection and so helps to minimize the non-articulated length of disposable tip assembly 205 distal to the last joint. In addition, the use of the one-quarter locking mechanism reduces the outer diameter of locking device 412 and so helps to reduce the outer maximum outer diameter of disposable tip of assembly 205.

Tip interface 245 includes an instrument tip 448. Instrument tip 448 has a central lumen 457 in which is positioned a grip actuator element 446. A distal end of instrument tip 448 includes an orientation alignment feature 449, in this example, includes flat surface 449A. A corresponding orientation alignment feature (not visible in FIG. 4A) is provided at the proximal end of clevis 407. The two orientation alignment features mate such that when instrument tip 448 is affixed to disposable tip assembly 205, disposable tip assembly 205 is properly oriented on reusable surgical instrument portion 204.

Proximal to flat surface 449A on instrument tip 448, in this aspect, is a lock interface element, e.g., a female bayonet receptacle 448B. In one aspect, instrument tip 448 is made of an electrically non-conducting rigid material such the glass-filled polyphthalamide described above. If electrical arc tracking is not of concern, an alternative material is an organic polymer thermoplastic such as polyether ether ketone (PEEK). Also, if electrical isolation is not needed, instrument tip 448 could be made from a medical grade stainless steel.

In one aspect, the maximum diameter of orientation alignment feature 449 is 0.160 inches (4.06 mm) and the flat surface has a length in the longitudinal direction of 0.065 inches (1.65 mm) and a length in a direction perpendicular to the longitudinal direction of 0.068 inches (1.72 mm). An outer diameter of instrument tip 448 in the region of receptacle 448B is 0.215 inches (5.45 mm). Lumen 457 has an inner diameter of 0.10 inches (2.54 mm). As noted previously, the citation of particular materials and sizes is illustrative only and is not intended to be limiting to these particular materials and sizes.

Grip actuator element 446 includes a grip drive element 458, sometimes referred to as element 458, which is mounted in a lumen of a grip actuator insulator 453. Grip actuator insulator 453 slides longitudinally in central lumen 457 of instrument tip 448. The outer surface of grip actuator insulator 453 has a dumbbell shape, e.g., a central portion of the outer surface is depressed relative to the proximal and distal end portions of the outer surface.

A seal 454 extends around the central portion of the outer surface of grip actuator insulator 453. Seal 454 forms a seal between the inner wall of instrument tip 448 and grip actuator insulator 453. Thus, seal 454 isolates the wrist and main tube from electrically hot fluid that passes through disposable tip assembly 205. Seal 454 moves parallel to a longitudinal axis 492 of instrument tip 448 and so helps to reduce the non-articulated length distal to the last joint. In one aspect, seal 454 is made from the tear-resistant silicone elastomer that was described above. In this aspect, grip actuator insulator 453 is made from the glass-filled polyphthalamide described above.

In this aspect, grip drive element 458 is made of 17-4 stainless steel, which was described above. Grip drive element 458 has a central lumen extending from a proximal end of element 458. A distal portion of element 458 is a socket 447. Socket 447 is sized and configured to mate with ball 409.

A hypotube 455, e.g., an aglet, is crimped to a distal end of tendon 452. The hypotube and tendon combination is inserted in the central lumen of grip drive element 458 and is then laser welded to grip drive element 458. Alternatively, hypotube 455 could be crimped into place. Grip actuator insulator 453 is bonded to grip drive element 458. In another aspect, grip actuator insulator 453 is overmolded on grip drive element 458 after hypotube 455 is fixed to grip drive element 458.

In one aspect tendon 452 is a braided tungsten cable contained in an electrically insulating sheath (jacket). In one aspect, the sheath is a tube of a fluoropolymer such as ethylene tetrafluorethylene (ETFE). In addition to the insulating properties, the sheath increases the push/pull stiffness of tendon 452 and so helps to reduce buckling of tendon 452.

A wrist-disposable tip adapter 450 is affixed to the proximal end of instrument tip 448. Tendon 452 with sheath 456 passes through a guide 451 that is mounted in a central lumen of wrist-disposable tip adapter 450. In one aspect, guide 451 is implemented as a flexible bushing. Guide 451 is molded using a fluorpolymer such as polytetrafluoroethylene (PTFE) or fluorinated ethylene propylene (FEP).

In FIGS. 4A and 4B, a knob (FIG. 11) or a lever has been moved that in turn moves tendon 452 in the distal direction so that socket 447 is pushed beyond the distal end of instrument tip 448. As indicated above, locking tip cover 410 has also been moved in the distal direction until clevis 407 contacts a stop, e.g., a proximal side surface of external cover 411. This exposes ball 409. A user can see the two quick connect/disconnect components, ball 409 and socket 447 that must be mated to start the attachment of disposable tip assembly 205 to reusable instrument portion 204.

In FIGS. 5A and 5B, ball 409 has been placed in socket 447. In this example, ball 409 is positioned in socket 447 at an angle to longitudinal axis 492 of instrument tip 448. In FIGS. 6A and 6B with ball 409 in socket 447, disposable tip assembly 205 is moved so that longitudinal axis 491 of tip 205 is aligned with longitudinal axis 492 of instrument tip 448.

When tendon 452 in FIG. 6A is pulled in the proximal direction, disposable tip assembly 205 is pulled in the proximal direction. As disposable tip assembly 205 moves in the proximal direction, orientation alignment feature 449 is aligned with the corresponding feature in disposable tip assembly 205. The alignment of orientation alignment feature 449 with the corresponding feature in disposable tip assembly 205 ensures that the two components are properly oriented.

Hence, as illustrated in FIGS. 7A and 7B, when grip actuator insulator 453 reaches the limit of travel towards the proximal end of central lumen 457, ball 409 and socket 447, a proximal portion of rod 408R, and grip actuator element 446 are positioned inside central lumen 457. The orientation alignment features have assured that the proximal end of clevis 407 has mated with the distal end of instrument tip 448.

Figure 7D:
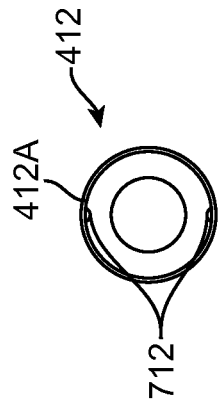
FIG. 7D is an end view of the locking device of FIG. 4A from the proximal direction.
Figure 7C:
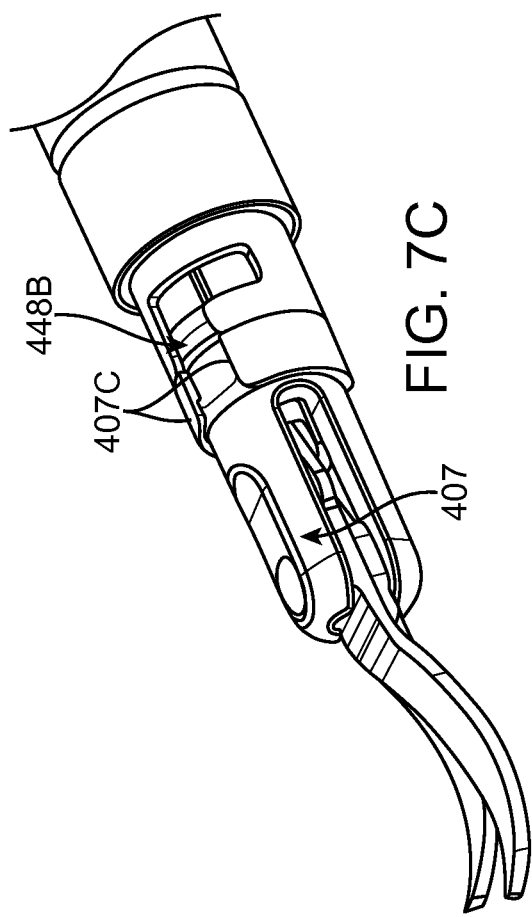
FIG. 7C is an illustration of the apparatus in FIG. 7A with the external cover removed.

FIG. 7C is a prospective view of the configuration in FIGS. 7A and 7B with locking tip cover 410 removed. FIG. 7C shows that after the mating, bayonet guide feature 407C of clevis 407 aligned with a first portion of bayonet female receptacle 448B on instrument tip 448. One protrusion 712 (FIG. 7D) of locking device 412 is slid through the channel formed by bayonet guide feature 407C of clevis 407 and the first portion of bayonet female receptacle 448B until shoulder 407B of clevis 407 abuts shoulder 412B of locking device 412. Locking device 412 is then rotated clockwise, in this aspect, into a second portion of bayonet female receptacle 448B. The rotation locks locking tip cover 410 to tip interface 245 at the distal end of reusable instrument portion 204.

Figure 8:
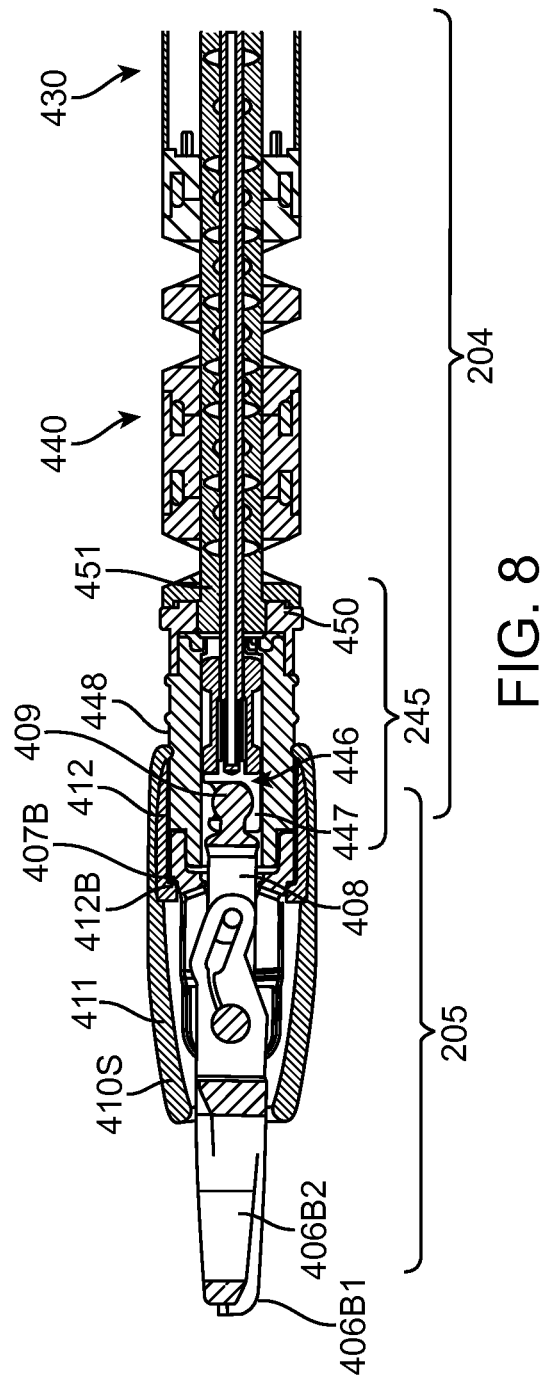
FIG. 8 is a cutaway view of the apparatus of FIG. 2.

As indicated above, FIG. 2 is an illustration of locking tip cover 410 mounted on and locked to reusable instrument portion 204. FIG. 8 is a cross-sectional illustration of FIG. 2. FIG. 8 shows a mechanical connection between blades 406B1, 406B2, actuator rod assembly 408, grip actuator element 446, and tendon 452. This mechanical connection permits mechanical actuation of blades 406B1, 406B2, as described more completely below, by push-pull action of tendon 452.

When, for example, disposable blade assembly 206 is a disposable monopolar curved scissor assembly, an electrical connection exists between disposable tip assembly 205 and reusable instrument portion 204. This electrical connection is made through the ball and socket connection used for the mechanical connection and actuation. To maintain isolation between blades 406B1, 406B2 and the instrument joints, instrument tip 448 is made from an electrically non-conductive material. Additionally, while not required, making clevis 407 from an electrically non-conductive material lengthens any potential arc paths between the exposed portion of blades 406B 1, 406B2 and the instrument joints. Thus, the locked combination of disposable tip assembly 205 and disposable tip interface 245 provides both an electrical connection and electrical isolation between components.

The locked combination of disposable tip assembly 205 and disposable tip interface 245 also provides an insulating seal 454 that creates an isolation barrier for fluids between the electrically hot active electrode and the patient. In one aspect, external cover 411 provides an overmolded seal 410S at the proximal end of disposable tip interface 245. Seal 410S is formed between a lip of cover 411 and an outer circumferential surface of instrument tip 448.

In FIG. 8, tendon guide 451 is shown in greater detail. FIG. 8 shows that guide 451 extends from the lumen in wrist-disposable tip adapter 450 proximally through wrist 240 and main tube 230. In one aspect, tendon guide 451 extends proximally to the proximal end of main tube 230.

In FIGS. 9A and 9B, tendon 452 is pushed distally by an actuator drive assembly (not shown). The motion of tendon 452 pushes grip actuator element 446 distally in central lumen 457 of instrument tip 448. The motion of grip actuator element 446 pushes actuator rod assembly 408 distally. Pin 408P slides in the slots of blades 406B1, 406B2, which in turn causes blades 406B1, 406B2 to pivot about pin 407P and open as shown in FIGS. 9A and 9B. When tendon 452 is pulled proximally, blades 406B1, 406B2 close.

FIGS. 10A to 10D are cross sectional drawings of tip interface 345 and disposable tip assembly 305. FIGS. 10A to 10D illustrate the connection of tip interface 345 to disposable tip assembly 305. Although, it is not shown in these drawings, tip interface 345 is located at the distal end of a reusable surgical instrument portion similar to reusable surgical instrument portion 204.

Figure 10A:
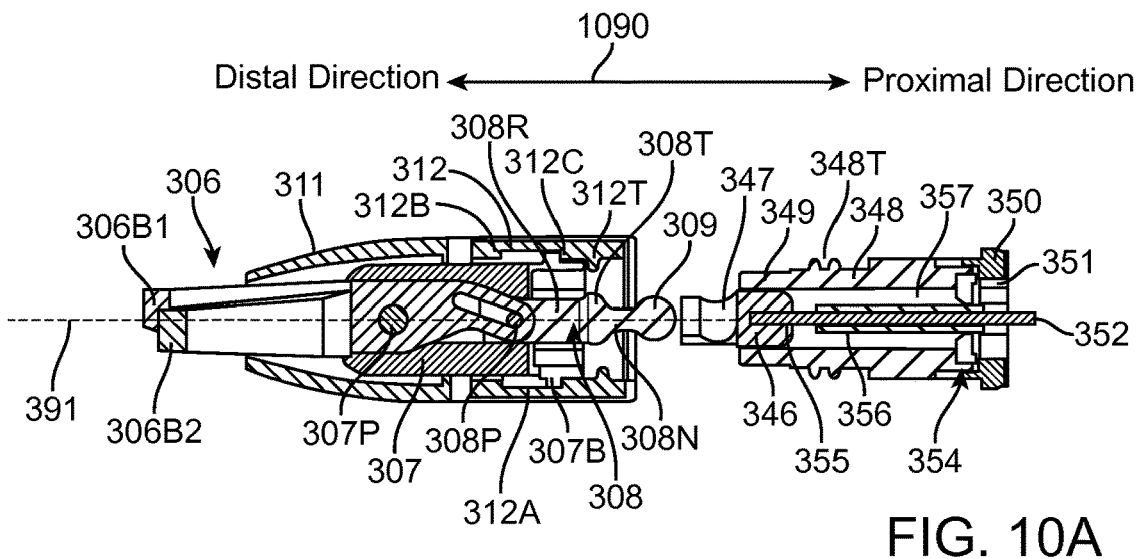
FIGS. 10A to 10D are cutaway illustrations of stages in attaching a disposable instrument tip assembly to a reusable instrument portion.

In FIG. 10A, disposable tip assembly 305 (FIG. 3) is positioned for connection to tip interface 345. Grip actuator element 346 (FIG. 10A) has been slid in a central lumen 357 of instrument tip 348 so that socket 347 is positioned distally of the distal end of instrument tip 348. In FIGS. 10A to 10D, the distal direction is towards the tips of blades 306B1 and 306B2 in disposable blade assembly 306 and the proximal direction is towards wrist-disposable tip adapter 350 as show by arrow 1090. In one aspect, grip actuator element 346 is moved about 0.18 inches (4.57 mm) from a normal closed position of grip actuator element 346 (see FIG. 10D) to receive ball 309 of disposable tip assembly 305.

As shown in FIG. 10A, disposable blade assembly includes two blades 306B1 and 306B2 that are connected to clevis 307 by a first pin 307P. A second pin 308P is positioned in a slot in the proximal ends of blades 306B1 and 306B2 so that pin 308P moves in the slot to actuate the blades. Second pin 308P passes through and floats in a distal end a solid cylindrical rod 308R in actuator rod assembly 308.

In one aspect, blades 306B1 and 306B2 are monopolar curved blades equivalent to blades 406B1 and 406B2. Clevis 307 can be made of an electrically non-conducting material or an electrically conducting material. An electrically non-conducing material suitable for clevis 307 is the glass-filled polyphthalamide described above. An electrically non-conducting clevis 307 lengthens any possible unintended arc path from blades 306B1 and 306B2 and/or actuator rod assembly 308 to the patient when a voltage is applied to blades 306B1 and 306B2. An electrically conducting clevis 307 can be made of 17-4 stainless steel. However, any stainless steel that can be used in metal injection modeling could be used.

Actuator rod assembly 308 is made of 17-4 stainless steel and includes a solid cylindrical rod 308R with ball 309 at the proximal end of cylindrical rod 308R. In one aspect, the overall length of actuator rod assembly 308 is 0.34 inches (8.6 mm). The diameter of cylindrical rod 308R is 0.090 inches (2.28 mm) and the length is 0.34 inches (8.6 mm). In one aspect, ball 309 has a diameter of 0.070 inches (1.78 mm). There is a transition region 308T between neck region 308N and ball 309. Transition region 308T reduces the diameter of ball 309 to the diameter of cylindrical rod 308R.

Locking tip cover 310 provides both an electrically insulating seal component and an isolation barrier. The insulating seal component is a rigid, non-conductive component, i.e., locking device 312, which locks disposable tip assembly 305 to instrument tip 348 and an overmolded seal, e.g., external cover 311.

In one aspect, locking device 312 is molded using a glass-filled polyphthalamide (PPA) such as that described above. Other suitable material include PEI (ULTEM®), as described above. In one aspect, external cover 311 is made of a silicone rubber with high tear strength, e.g., a tear-resistant silicone elastomer. The silicone rubber is biocompatible and withstands at least 4 kV. An example of such a silicone rubber is sold by Dow Corning Corporation as Silastic® Biomedical Grade ETR Elastomer Q7-4750. Other suitable materials include flexible, medical grade elastomers including polyurethane thermoplastic elastomers such as that Pellethane polyurethane thermoplastic elastomer provided by The Upjohn Company. Any materials and any dimensions provided herein are illustrative only and are not intended to be limiting to those specific dimensions and materials.

Disposable tip assembly 305 has a longitudinal axis 391. Locking device 312 is free to rotate around longitudinal axis 391 and so free to rotate around clevis 307. Locking device 312 has a circumferential interior surface 312A that is flat in the cross-sectional view of FIG. 10A and extends distally from a proximal shoulder 312C of locking device 312 to a distal shoulder 312B. In this aspect, both shoulders 312B and 312C are formed perpendicular to interior surface 312A. The two shoulders and the flat surface define a groove in the interior surface of locking device 312.

Figure 10B:
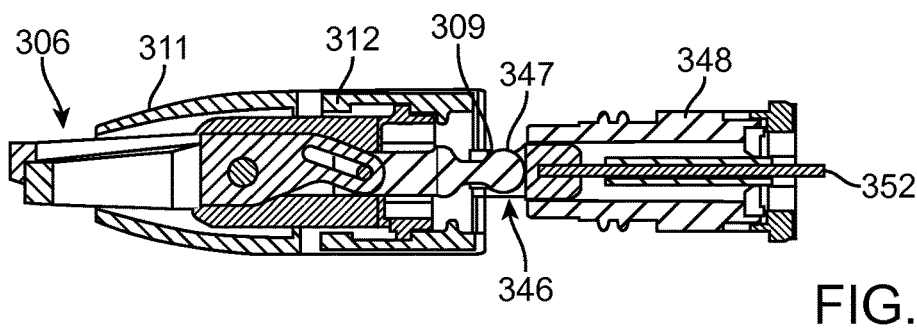

A length of interior surface 312A substantially parallel to longitudinal axis 391 is selected based on at least two criteria. First, the length in the proximal direction is chosen so that when locking tip cover 310 is moved distally and the protrusion 307B on the outer surface of clevis 307 abuts shoulder 312C, ball 309 extends beyond the proximal end of external cover 311 as shown in FIGS. 10A and 10B. Second, when external cover is moved proximally so that assembly 305 is mounted on and affixed to reusable surgical instrument portion 304, as described below, the length is such that protrusion 307B abuts shoulder 312B (see FIG. 10D).

It should be understood that the features of surface 312A and shoulders 312B and 312C shown in FIG. 10A are illustrative only and are not intended to be limiting. In general, inner surface 312A and shoulders 312B and 312C of locking device 312 are selected to work with clevis 307 to provide the functionally just described. In general, shoulders on both locking device 312 and clevis 307 position clevis 307 in the proper location as the two components are drawn together and locking device 312 is actuated.

Tip interface 345 includes an instrument tip 348. Locking device 312 includes a thread 312T that is used to attach disposable tip assembly 305 to threads 348T on the outer surface of instrument tip 348. Instrument tip 348 has a central lumen 357 in which is positioned a grip actuator element 346. A distal end of instrument tip 348 includes an orientation alignment feature 349, in this example, includes flat surface 349A (not visible in FIG. 10A). A corresponding orientation alignment feature is provided at the proximal end of clevis 307. The two orientation alignment features mate such that when instrument tip 348 is affixed to disposable tip assembly 305, disposable tip assembly 305 is properly oriented on the reusable surgical instrument portion.

Grip actuator element 346 slides longitudinally in lumen 357 of instrument tip 348. In this aspect, grip actuator element 346 is made of 17-4 stainless steel. A distal portion of element 346 is a socket 347. Socket 347 is sized and configured to mate with ball 309.

A hypotube 355, e.g., an aglet, is crimped to a distal end of tendon 352. The hypotube and tendon combination is inserted in a central lumen of grip actuator element 346 and is then laser welded to grip actuator element 346. Alternatively, hypotube 355 could be crimped in place in grip actuator element 346.

In one aspect tendon 352 is a braided tungsten cable contained in an electrically insulating sheath (jacket). In one aspect, the sheath is a tube of a fluorpolymer such as ETFE. In addition to the insulating properties, the sheath increases the push/pull stiffness of tendon 352 and so helps to reduce buckling of tendon 352.

A wrist-disposable tip adapter 350 is affixed to the proximal end of instrument tip 348. A rigid non-conductive seal 354 is mounted between the proximal end of tip 348 and wrist-disposable tip adapter 350 to seal central lumen 357. Tendon 352 with sheath 356 passes through seal 354 and a guide 351 that is mounted in a central lumen of wrist-disposable tip adapter 350. In one aspect, guide 351 is implemented as a flexible bushing. Guide 351 is molded using a fluoropolymer such as PTFE or FEP.

In FIGS. 10A and 10B, a knob (FIG. 11) or a lever has been moved that in turn pushes tendon 352 in the distal direction so that socket 347 extends beyond the distal end of instrument tip 348. As indicated above, locking tip cover 310 has also been moved in the distal direction to expose ball 309. Thus, allows a user to see the two quick connect/disconnect components, ball 309 and socket 347 that must be mated to start the attachment of disposable tip assembly 305 to the reusable instrument portion.

Figure 10C:
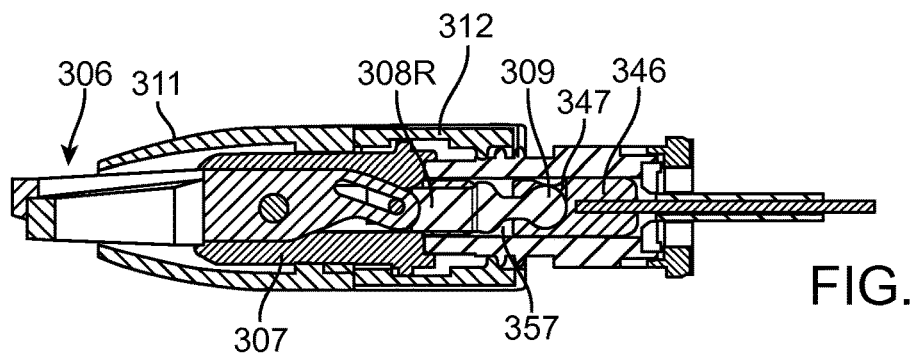

In FIG. 10B, ball 309 has been placed in socket 347. In FIG. 10C with ball 309 in socket 347, tendon 352 is pulled in the proximal direction, which in turn pulls disposable tip assembly 305 in the proximal direction. As disposable tip assembly 305 moves in the proximal direction, orientation alignment feature 349A is aligned with the corresponding features in disposable tip assembly 305. The alignment of orientation alignment feature 349A with the corresponding features in disposable tip assembly 305 ensures that the two components are properly oriented.

Hence, as illustrated in FIG. 10C, when grip actuator element 346 reaches the limit of travel towards the proximal end of central lumen 357, ball 309 and socket 347, grip actuator element 346, and a proximal portion of cylindrical rod 308R of actuator rod assembly 308 are positioned in central lumen 357. The proximal end of clevis 307 has mated with the distal end of instrument tip 348.

Figure 10D:
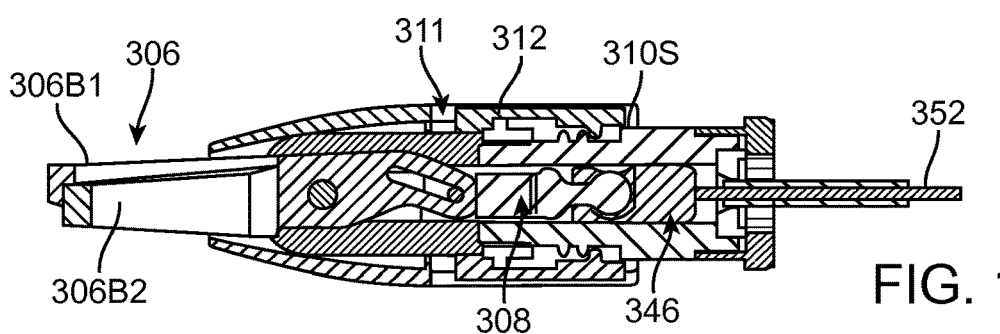

In FIG. 10D, locking device 312 has been screwed onto instrument tip 348 so that disposable tip assembly 305 is mounted on and affixed to tip interface 345. This locks disposable blade assembly 306 in place.

In this configuration, there is a mechanical connection between blades 306B1, 306B2, actuator rod assembly 308, grip actuator element 346, and tendon 352. This mechanical connection permits mechanical actuation of blades 306B1, 306B2, in a manner similar to that described above for blades 406B1, 406B2.

When, for example, disposable blade assembly 306 is a disposable monopolar curved scissor assembly, an electrical connection exists between disposable tip assembly 305 and the reusable instrument portion. This electrical connection is made through the ball and socket connection used for the mechanical connection and actuation. To maintain isolation between blades 306B1, 306B2 and the instrument joints, instrument tip 348 is made from an electrically non-conductive material. Additionally, while not required, making clevis 307 from an electrically non-conducting material lengthens any potential arc paths between the exposed portion of blades 306B1, 306B2 and the patient. Thus, the locked combination of disposable tip assembly 305 and disposable tip interface 345 provides both an electrical connection and isolation between components.

The locked combination of disposable tip assembly 305 and disposable tip interface 345 also provides an insulating seal 354 that creates an isolation barrier for fluids between the electrically hot active electrode and the patient. In one aspect, external cover 311 provides an overmolded seal 310S at the proximal end of disposable tip assembly 305. Seal 310S is formed between a lip of cover 311 and an outer circumferential surface of instrument tip 348.

Figure 11:
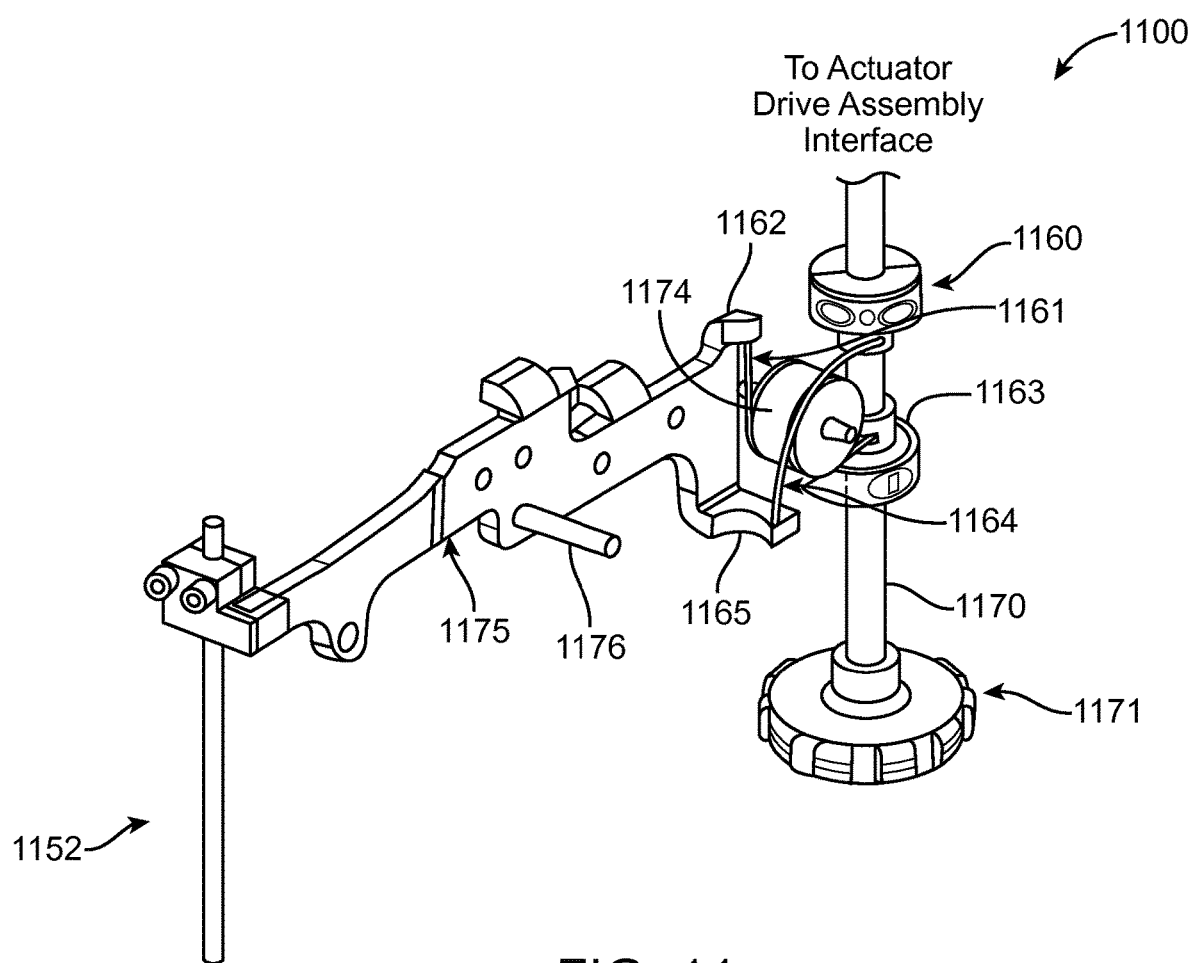
FIG. 11 is an illustration of a push-pull drive assembly.

FIG. 11 is an illustration of one aspect of a rotary grip drive assembly 1100, which is an example of a push-pull drive assembly. Rotating knob 1171 in a first direction (clockwise) causes sheathed tendon 1152 to move in a first linear direction (down in FIG. 11). Rotating knob 1171 in a second direction (counter clockwise) opposite the first direction causes sheathed tendon 1152 to move in a second linear direction (up in FIG. 11) that is opposite in direction to the first linear direction. Movement of tendon 1152 in the first linear direction results in grip actuator element 346 (FIG. 10A) in one aspect, and grip actuator element 446 (FIG. 4B) in another aspect, being pushed in the distal direction. Conversely, movement of tendon 1152 in the second linear direction results in grip actuator element 346 in one aspect, and grip actuator element 446 in another aspect, being pulled in the proximal direction.

Typically, knob 1171 is used to position the grip actuator element for engaging and disengaging the actuator rod assembly in the disposable tip assembly. When the disposable tip assembly is mounted on and locked to the reusable instrument portion, an actuator drive assembly is used to control the movement of sheathed tendon 1152 in response to input from a user at a master control station.

In FIG. 11, a drive shaft 1170 has a first end configured to couple to the actuator drive assembly. The particular configuration used to couple to the actuator drive assembly depends on the system in which rotary grip drive assembly 1100 is included. Knob 1171 is mounted on a second end of drive shaft 1170. Two capstans 1160 and 1163 are also mounted on drive shaft 1170.

A first cable 1161 has a first end affixed to capstan 1163. Cable 1161 passes around pulley 1174 and a second end of cable 1161 is attached to a first arm 1162 at a first end of lever 1175. A second cable 1164 has a first end affixed to capstan 1160. Cable 1164 passes over pulley 1174 and a second end of cable 1164 is attached to a second arm 1165 at the first end of lever 1175. First arm 1162 is opposite and removed from second arm 1165 at the first end of lever 1175.

Lever 1175 is mounted on a rod 1176 that functions as the fulcrum (pivot point) for lever 1175. Sheathed tendon 1152 is affixed to a second end of lever 1175. In this example, lever 1175 is a Class 1 lever because the fulcrum is between the effort (the forces supplied by cables 1161 and 1164) and the load (sheathed tendon 1152). Sheathed tendon 1152, in this aspect, moves in a direction opposite to the direction of the force on the first end of lever 1175.

While in this example, lever 1175 is implemented as a Class 1 lever, this is illustrative only and is not intended to be limiting. In other aspects, a Class 2 lever or a Class 3 lever could be used. For a Class 2 lever, the load is between the fulcrum and the effort, and for a Class 3 lever, the effort is between the fulcrum and the load.

As used herein, "first," "second," and "third" are adjectives used to distinguish between different components or elements. Thus, "first," "second," and "third" are not intended to imply any ordering of the components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures were turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

I claim:

1. An apparatus comprising:
an end effector assembly comprising an end effector body assembly and an end effector, the end effector body assembly defining a longitudinal axis and comprising a protrusion extending perpendicularly relative to the longitudinal axis;
an actuator rod assembly connected to the end effector assembly to transfer a force from the actuator rod assembly to the end effector assembly; and
a surgical instrument tip assembly surrounding at least a portion of the end effector assembly, the surgical instrument tip assembly comprising a locking tip cover;
the locking tip cover comprising an external cover and a locking device;
the external cover comprising a proximal end portion;
the locking device being mounted inside the proximal end portion of the external cover;
the locking device comprising a first shoulder portion, a second shoulder portion, and a circumferential interior surface;
the circumferential interior surface extending from the first shoulder portion to the second shoulder portion, the circumferential interior surface comprising a first diameter, at least one of the first shoulder portion and the second shoulder portion defining a second diameter, and the first diameter being larger than the second diameter;
the locking device being movably mounted on the end effector body assembly to move relative to the end effector body assembly along the longitudinal axis, the protrusion riding along the circumferential interior surface between the first shoulder portion and the second shoulder portion between a distal travel limit and a proximal travel limit;
a portion of the actuator rod assembly extending beyond the proximal end portion of the external cover when the first shoulder portion is engaged with the protrusion; and
the portion of the actuator rod assembly being within the proximal end portion of the external cover when the second shoulder portion is engaged with the protrusion.

2. The apparatus of claim 1:
the locking device comprising an inner wall defining a central lumen;
the end effector body assembly being enclosed within said external cover and being mounted in the central lumen of the locking device so that the locking device has two degrees of freedom relative to the end effector body assembly; and
the actuator rod assembly comprising a connection element at a proximal end of the actuator rod assembly.

3. The apparatus of claim 2:
the end effector comprising a blade set; and
the end effector body assembly comprising a clevis.

4. The apparatus of claim 3, the blade set comprising monopolar-curved scissors.

5. The apparatus of claim 2, the connection element comprising a ball configured to mate with a socket of a surgical instrument.

6. The apparatus of claim 2, further comprising:
a surgical instrument comprising a tip interface, the tip interface comprising an instrument tip and a grip actuator element slidably positioned within a central lumen of the instrument tip;
wherein:
the connection element of the actuator rod assembly is a first connection element;
the instrument tip comprises a distal end and a lock interface element; and
the grip actuator element comprises a second connection element, the second connection element being configured to mate with the first connection element.

7. The apparatus of claim 6:
the first connection element comprising a ball; and
the second connection element comprising a socket configured to receive the ball.

8. The apparatus of claim 6, the surgical instrument further comprising a tendon having a first end coupled to the second connection element.

9. The apparatus of claim 8:
the tendon comprising an electrically conductive material; and
the second connection element comprising an electrically conductive material.

10. The apparatus of claim 6, the tip interface further comprising a seal mounted on a proximal end of the instrument tip.

11. The apparatus of claim 6, the tip interface further comprising a seal mounted on an outer circumferential surface of the grip actuator element.

12. The apparatus of claim 6, the lock interface element comprising a female portion of a bayonet locking mechanism.

13. The apparatus of claim 6, the lock interface element comprising a thread on an outer surface of the instrument tip.

14. The apparatus of claim 6, a proximal end of the external cover comprising a lip, and the lip forming a seal with the instrument tip when the surgical instrument tip assembly is locked to the surgical instrument.

15. The apparatus of claim 1:
the actuator rod assembly comprising an electrically conductive material; and
the locking tip cover comprises an electrically non-conductive material.

16. The apparatus of claim 1, the locking device comprising a male portion of a bayonet locking mechanism.

17. The apparatus of claim 1, the locking device comprising an inner wall and a thread extending from the inner wall.

18. The apparatus of claim 1, the external cover comprising an electrically non-conductive material.

19. The apparatus of claim 1, the external cover comprising a material molded over the locking device.

20. The apparatus of claim 1, wherein:
the distal travel limit is defined by the protrusion abutting the first shoulder portion such that the first shoulder portion prevents the protrusion from moving past the distal travel limit; and the proximal travel limit is defined by the protrusion abutting the second shoulder portion such that the second shoulder portion prevents the protrusion from moving past the proximal travel limit.

* * * * *